US011819504B2

(12) United States Patent
Tomarin et al.

(10) Patent No.: US 11,819,504 B2
(45) Date of Patent: Nov. 21, 2023

(54) METHODS AND COMPOSITIONS TO INCREASE HAIR GROWTH AND/OR PREVENT HAIR LOSS

(71) Applicant: HAIR PLUS HEALTH LLC, Dalton, GA (US)

(72) Inventors: Seymour Aaron Tomarin, Dalton, GA (US); James William Richards, Chatsworth, GA (US)

(73) Assignee: ATTAIN HEALTH INC., Dalton, GA (US)

( * ) Notice: Subject to any disclaimer, the term of this patent is extended or adjusted under 35 U.S.C. 154(b) by 326 days.

(21) Appl. No.: 17/271,387

(22) PCT Filed: Aug. 26, 2019

(86) PCT No.: PCT/US2019/048156
§ 371 (c)(1),
(2) Date: Feb. 25, 2021

(87) PCT Pub. No.: WO2020/046820
PCT Pub. Date: Mar. 5, 2020

(65) Prior Publication Data
US 2021/0186968 A1    Jun. 24, 2021

Related U.S. Application Data

(60) Provisional application No. 62/722,980, filed on Aug. 26, 2018.

(51) Int. Cl.
| A61K 31/506 | (2006.01) |
| A61K 9/00 | (2006.01) |
| A61K 31/194 | (2006.01) |
| A61K 31/58 | (2006.01) |
| A61K 47/14 | (2017.01) |
| A61K 47/24 | (2006.01) |

(52) U.S. Cl.
CPC .......... *A61K 31/506* (2013.01); *A61K 9/0014* (2013.01); *A61K 31/194* (2013.01); *A61K 31/58* (2013.01); *A61K 47/14* (2013.01); *A61K 47/24* (2013.01)

(58) Field of Classification Search
None
See application file for complete search history.

(56) References Cited

U.S. PATENT DOCUMENTS

| 5,183,817 | A | 2/1993 | Bazzano |
| 6,358,541 | B1 | 3/2002 | Goodman |
| 6,451,300 | B1 | 9/2002 | Dunlop et al. |
| 8,303,997 | B2 | 11/2012 | Mailland et al. |
| 8,834,940 | B2 | 9/2014 | Trigiante |
| 8,871,811 | B2 | 10/2014 | Banov et al. |
| 8,906,397 | B2 | 12/2014 | Banov et al. |
| 9,956,156 | B2 | 5/2018 | Wu |
| 2002/0035070 | A1 | 3/2002 | Gardlik et al. |
| 2002/0119174 | A1 | 8/2002 | Comstock et al. |
| 2007/0086972 | A1 | 4/2007 | Birnbaum |
| 2008/0051351 | A1 | 2/2008 | Ghisalberti |
| 2008/0152731 | A1 | 6/2008 | Trigiante |
| 2008/0160093 | A1 | 7/2008 | Scott et al. |
| 2012/0258059 | A1 | 10/2012 | Iwama et al. |
| 2014/0079686 | A1 | 3/2014 | Barman et al. |
| 2014/0377384 | A1 | 12/2014 | Trigiante |
| 2016/0213757 | A1 | 7/2016 | Edelson et al. |
| 2016/0346183 | A1 | 12/2016 | Sekhavat |
| 2017/0181948 | A1 | 6/2017 | Wu |
| 2018/0193236 | A1 | 7/2018 | Son et al. |
| 2019/0343835 | A1 | 11/2019 | Nava et al. |
| 2020/0095206 | A1 | 3/2020 | Markowitz et al. |
| 2020/0215007 | A1 | 7/2020 | Wang et al. |
| 2020/0241958 | A1 | 7/2020 | Shin |

FOREIGN PATENT DOCUMENTS

| CA | 3036692 A1 | 9/2017 |
| WO | 2006096461 A2 | 9/2006 |
| WO | 2014184173 A1 | 11/2014 |
| WO | 2018151838 A1 | 8/2018 |

OTHER PUBLICATIONS

Extended European Search Report for Application 19854761.4 dated May 11, 2022.
Examination Report for Australian application No. 2019329703 dated Feb. 28, 2022.
Harcha, Walter "A randomized, active- and placebo-controlled study of the efficacy and safety of different doses of dutasteride versus placebo and finasteride in the treatment of male subjects with androgenetic alopecia" J Am Acad Dermatol vol. 70, No. 3. Mar. 2014.
Elsherbeny H, Mohamed HA, Zaky MS. Evaluation of The Role of Topical Cetirizine 1% in Treatment of Male Androgenetic Alopecia. IJMA 2020; 2[4]: 793-797. DOI: 10.21608/IJMA.2020.34317.1142.
Price, Vera H. "Treatment of Hair Loss" The New England Journal of Medicine; Drug Therapy. vol. 341 No. 13, Sep. 23, 1999.

(Continued)

*Primary Examiner* — Nannette Holloman
(74) *Attorney, Agent, or Firm* — THOMAS | HORSTEMEYER, LLP

(57) ABSTRACT

In one aspect, the disclosure relates to topical formulations, methods of making same, and methods of treating hair loss using same. In an aspect, the present disclosure pertains to topical formulations for treatment of hair loss and/or to increase hair growth, the formulation comprising: a therapeutic composition comprising therapeutically effective amounts of azelaic acid, minoxidil, finasteride, and duasteride; and one or more compounding agents. In a further aspect, the present disclosure pertains to a method of treating hair loss by applying a disclosed topical formulation. In a further aspect, the present disclosure pertains to a method of enhancing hair grow by applying a disclosed topical formulation. This abstract is intended as a scanning tool for purposes of searching in the particular art and is not intended to be limiting of the present disclosure.

26 Claims, No Drawings

(56) References Cited

OTHER PUBLICATIONS

A. Rossi, D. Campo, M. C. Fortuna, V. Garelli, G. Pranteda, G. De Vita, L. Sorriso-Valvo, D. Di Nunno & M. Carlesimo (2017): A preliminary study on topical cetirizine in the therapeutic management of androgenetic alopecia, Journal of Dermatological Treatment, DOI: 10.1080/09546634.2017.1341610.
International Search Report and Written Opinion for PCT/US19/48156 dated Nov. 18, 2019.
Australian Examination Report for Application No. 2019329703 dated Feb. 28, 2022.
Indian Examination Report for Application No. 202127013113 dated Feb. 24, 2022.
Canadian Examination Report for Application No. 3,110,856 dated Apr. 20, 2022.

METHODS AND COMPOSITIONS TO INCREASE HAIR GROWTH AND/OR PREVENT HAIR LOSS

CROSS-REFERENCE TO RELATED APPLICATIONS

This application claims the benefit of U.S. Provisional Application No. 62/722,980, filed on Aug. 26, 2018, which is incorporated herein by reference in its entirety.

BACKGROUND

Dermatologists recognize many different types of hair loss, the most common by far being "androgenetic alopecia" wherein human males or females begin losing scalp hair at the temples and on the crown of the head. While this type of hair loss is largely confined to males, hence its common name "male pattern baldness," it is not unknown in women.

Androgenetic alopecia (AGA) is the most common form of hair loss, affecting approximately 50 percent of all men and women by the age of 50. Common treatments for androgenetic alopecia include hair follicle transplants, topical therapies, and orally prescribed anti-androgens. The hyperandrogenic stimulation that causes androgenetic alopecia also produces other undesirable physiological symptoms including acne vulgaris, benign prostatic hyperplasia, female hirsutism, and seborrhea.

Several anti-alopecia agents such as minoxidil and cyoctol have gained attention. However, these anti-alopecia agents are only minimally effective in some cases and/or can cause adverse dermatological or systemic reactions. In particular, single agent formulations may have limited efficacy in many subjects.

It is also known that many of the currently available formulations have to be applied topically two or more times in the course of a 24 hour period. The frequency of application can mitigate the efficacy of treatment due to missed applications and also lead to user frustration and/or error.

In addition, many conventional formulations have undesirable side effects of drying hair and/or scalp, frizzing or kinking of the hair, scalp itching or irritation and undesirable cosmetic effects such as slow drying upon application leading to an extended time period of "wet" hair. An important characteristic of a hair treatment formulation should be that it provides not only reduced hair loss and/or increased hair growth, but also healthy looking hair and scalp.

Thus, despite advances in research directed to treat hair loss and/or increase hair growth, there is still a scarcity of topical treatment compositions and methods that are potent, efficacious, and require minimal frequency of application, while at the same time minimizing undesirable side-effects and providing healthy looking hair and/or scalp. These needs and other needs are satisfied by the present disclosure.

SUMMARY

In accordance with the purpose(s) of the present disclosure, as embodied and broadly described herein, the disclosure, in one aspect, relates to topical formulations, methods of making same, and methods of treating hair loss using same.

In an aspect, the present disclosure pertains to topical formulations for treatment of hair loss and/or to increase hair growth, the formulation comprising: a therapeutic composition comprising therapeutically effective amounts of azelaic acid, minoxidil, finasteride, and duasteride; and one or more compounding agents.

In a further aspect, the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract.

In a further aspect, the present disclosure pertains to a method of treating hair loss by applying a disclosed topical formulation.

In a further aspect, the present disclosure pertains to a method of enhancing hair grow by applying a disclosed topical formulation.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described aspects are usable in all aspects of the disclosure taught herein. Furthermore, the individual features of the dependent claims, as well as all optional and preferred features and modifications of the described aspects are combinable and interchangeable with one another.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Many modifications and other aspects disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific aspects disclosed and that modifications and other aspects are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure.

Any recited method can be carried out in the order of events recited or in any other order that is logically possible.

That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of".

As used in the specification and the appended claims, the singular forms "a," "an" and "the" include plural referents unless the context clearly dictates otherwise. Thus, for example, reference to "a silicone base," "a gel base for gel-cream emulsions," or "a heavy cream base," including, but not limited to, two or more such silicone bases, gel bases for gel-cream emulsions, or heavy cream base, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about"

whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a therapeutic agent refers to an amount that is sufficient to achieve the desired improvement in clinical condition modulated by the formulation component, e.g. achieving the desired level of hair growth or mitigation of hair loss. The specific level in terms of wt % in a composition required as an effective amount will depend upon a variety of factors including the amount and type of therapeutic agent and formulation type, e.g., ointment, cream, gel, and the like.

As used herein, the terms "optional" or "optionally" means that the subsequently described event or circumstance can or cannot occur, and that the description includes instances where said event or circumstance occurs and instances where it does not.

Therapeutic agents should be understood to include the neutral forms of the drug and pharmaceutically acceptable forms thereof. "Pharmaceutically acceptable" refers to those compounds, materials, compositions, salts and/or dosage forms which, within the scope of sound medical judgment, are suitable for administration to patients without excessive toxicity, irritation, allergic response, or other problems or complications commensurate with a reasonable benefit/risk ratio. By "pharmaceutically acceptable forms" thereof is meant any pharmaceutically acceptable derivative or variation, including stereoisomers, stereoisomer mixtures, enantiomers, solvates, hydrates, isomorphs, polymorphs, pseudomorphs, salt forms and prodrugs. Preferably in some aspects, the pharmaceutically acceptable forms include salt forms. In other preferable aspects the pharmaceutically acceptable forms include, any stereoisomer or stereoisomeric mixture of the therapeutic agent.

Unless otherwise specified, temperatures referred to herein are based on atmospheric pressure (i.e. one atmosphere).

Disclosed Formulations

In various aspects, the present disclosure pertains to topical formulations for treatment of hair loss and/or to increase hair growth, the formulation comprising: a therapeutic composition comprising therapeutically effective amounts of azelaic acid, minoxidil, finasteride, and duasteride; and one or more compounding agents. Without wishing to be bound by a particular theory, it is believed that the disclosed combination of azelaic acid, minoxidil, finasteride, and duasteride in the disclosed amounts can have a synergistic effect with regard to increasing hair growth. Further, without wishing to be bound by a particular theory, it is believed that the disclosed combination of azelaic acid, minoxidil, finasteride, and duasteride in the disclosed amounts can have a synergistic effect with regard to mitigating or slowing hair loss. As used herein, the cream base is inclusive of a heavy cream base. It is understood that terms such as "cream base," "heavy cream base," "a gel base for gel-cream emulsions," and "silicone base" are intended to be in the context of pharmaceutically acceptable forms of a cream base," "heavy cream base," "a gel base for gel-cream emulsions," and "silicone base."

In a further aspect, the disclosed topical formulation comprising therapeutically effective amounts of azelaic acid, minoxidil, finasteride, and duasteride; and one or more compounding agents comprises therapeutically effective amounts of azelaic acid, minoxidil, finasteride, and duasteride as follows: about 0.100 wt % to about 0.500 wt % azelaic acid; about 10 wt % to about 20 wt % minoxidil; about 0.05 wt % to about 0.50 wt % finasteride; and about 0.001 wt % to about 0.030 wt % duasteride; wherein the wt % of a component is based on the total weight of the therapeutic composition; and one or more compound agents.

In a further aspect, the disclosed topical formulation comprising therapeutically effective amounts of azelaic acid, minoxidil, finasteride, and duasteride; and one or more compounding agents comprises therapeutically effective amounts of azelaic acid, minoxidil, finasteride, and duasteride as follows: about 0.300 wt % to about 0.400 wt % azelaic acid; about 12 wt % to about 17 wt % minoxidil; about 0.10 wt % to about 0.30 wt % finasteride; and about 0.005 wt % to about 0.015 wt % duasteride; wherein the wt % of a component is based on the total weight of the therapeutic composition; and one or more compounding agents.

In a further aspect, the disclosed topical formulation comprising therapeutically effective amounts of azelaic acid, minoxidil, finasteride, and duasteride; and one or more compounding agents comprises therapeutically effective amounts of azelaic acid, minoxidil, finasteride, and duasteride as follows: about 0.325 wt % azelaic acid; about 15 wt % minoxidil; about 0.20 wt % finasteride; and about 0.010 wt % duasteride; wherein the wt % of a component is based on the total weight of the therapeutic composition and one or more compounding agents.

In a further aspect, the disclosed topical formulation comprising therapeutically effective amounts of azelaic acid, minoxidil, finasteride, and duasteride; and one or more compounding agents comprises a therapeutically effective amount of azelaic acid, wherein the azelaic acid is present in an amount of about 0.100 wt %, about 0.105 wt %, about 0.110 wt %, about 0.115 wt %, about 0.120 wt %, about 0.125 wt %, about 0.130 wt %, about 0.135 wt %, about 0.140 wt %, about 0.145 wt %, about 0.150 wt %, about 0.155 wt %, about 0.160 wt %, about 0.165 wt %, about 0.170 wt %, about 0.175 wt %, about 0.180 wt %, about 0.185 wt %, about 0.190 wt %, about 0.195 wt %, about 0.200 wt %, about 0.205 wt %, about 0.210 wt %, about 0.215 wt %, about 0.220 wt %, about 0.225 wt %, about 0.230 wt %, about 0.235 wt %, about 0.240 wt %, about 0.245 wt %, about 0.250 wt %, about 0.255 wt %, about 0.260 wt %, about 0.265 wt %, about 0.270 wt %, about 0.275 wt %, about 0.280 wt %, about 0.285 wt %, about 0.290 wt %, about 0.295 wt %, about 0.300 wt %, about 0.305 wt %, about 0.310 wt %, about 0.315 wt %, about 0.320 wt %, about 0.325 wt %, about 0.330 wt %, about 0.335 wt %, about 0.340 wt %, about 0.345 wt %, about 0.350 wt %, about 0.355 wt %, about 0.360 wt %, about 0.365 wt %, about 0.370 wt %, about 0.375 wt %, about 0.380 wt %, about 0.385 wt %, about 0.390 wt %, about 0.395 wt %, about 0.400 wt %, about 0.405 wt %, about 0.410 wt %, about 0.415 wt %, about 0.420 wt %, about 0.425 wt %, about 0.430 wt %, about 0.435 wt %, about 0.440 wt %, about 0.445 wt %, about 0.450 wt %, about 0.455 wt %, about 0.460 wt %, about 0.465 wt %, about 0.470 wt %, about 0.475 wt %, about 0.480 wt %, about 0.485 wt %, about 0.490 wt %, about 0.495 wt %, about 0.500 wt %; or any range encompassed by the foregoing values; or any combination of the foregoing values.

In a further aspect, the disclosed topical formulation comprising therapeutically effective amounts of azelaic acid, minoxidil, finasteride, and duasteride; and one or more compounding agents comprises therapeutically effective amounts of minoxidil, wherein the minoxidil is present in an amount of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %, about 10.1 wt %, about 10.2 wt %, about 10.3 wt %, about 10.4 wt %, about 10.5 wt %, about 10.6 wt %, about 10.7 wt %, about 10.8 wt %, about 10.9 wt %, about 11.0 wt %, about 11.1 wt %, about 11.2 wt %, about 11.3 wt %, about 11.4 wt %, about 11.5 wt %, about 11.6 wt %, about 11.7 wt %, about 11.8 wt %, about 11.9 wt %, about 12.0 wt %, about 12.1 wt %, about 12.2 wt %, about 12.3 wt %, about 12.4 wt %, about 12.5 wt %, about 12.6 wt %, about 12.7 wt %, about 12.8 wt %, about 12.9 wt %, about 13.0 wt %, about 13.1 wt %, about 13.2 wt %, about 13.3 wt %, about 13.4 wt %, about 13.5 wt %, about 13.6 wt %, about 13.7 wt %, about 13.8 wt %, about 13.9 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %; or any range encompassed by the foregoing values; or any combination of the foregoing values.

In a further aspect, the disclosed topical formulation comprising therapeutically effective amounts of azelaic acid, minoxidil, finasteride, and duasteride; and one or more compounding agents comprises therapeutically effective amounts of minoxidil, wherein the finasteride is present in an amount of about 0.010 wt %, about 0.015 wt %, about 0.020 wt %, about 0.025 wt %, about 0.030 wt %, about 0.035 wt %, about 0.040 wt %, about 0.045 wt %, about 0.050 wt %, about 0.055 wt %, about 0.060 wt %, about 0.065 wt %, about 0.070 wt %, about 0.075 wt %, about 0.080 wt %, about 0.085 wt %, about 0.090 wt %, about 0.095 wt %, about 0.100 wt %, about 0.105 wt %, about 0.110 wt %, about 0.115 wt %, about 0.120 wt %, about 0.125 wt %, about 0.130 wt %, about 0.135 wt %, about 0.140 wt %, about 0.145 wt %, about 0.150 wt %, about 0.155 wt %, about 0.160 wt %, about 0.165 wt %, about 0.170 wt %, about 0.175 wt %, about 0.180 wt %, about 0.185 wt %, about 0.190 wt %, about 0.195 wt %, about 0.200 wt %, about 0.205 wt %, about 0.210 wt %, about 0.215 wt %, about 0.220 wt %, about 0.225 wt %, about 0.230 wt %, about 0.235 wt %, about 0.240 wt %, about 0.245 wt %, about 0.250 wt %, about 0.255 wt %, about 0.260 wt %, about 0.265 wt %, about 0.270 wt %, about 0.275 wt %, about 0.280 wt %, about 0.285 wt %, about 0.290 wt %, about 0.295 wt %, about 0.300 wt %, about 0.305 wt %, about 0.310 wt %, about 0.315 wt %, about 0.320 wt %, about 0.325 wt %, about 0.330 wt %, about 0.335 wt %, about 0.340 wt %, about 0.345 wt %, about 0.350 wt %, about 0.355 wt %, about 0.360 wt %, about 0.365 wt %, about 0.370 wt %, about 0.375 wt %, about 0.380 wt %, about 0.385 wt %, about 0.390 wt %, about 0.395 wt %, about 0.400 wt %, about 0.405 wt %, about 0.410 wt %, about 0.415 wt %, about 0.420 wt %, about 0.425 wt %, about 0.430 wt %, about 0.435 wt %, about 0.440 wt %, about 0.445 wt %, about 0.450 wt %, about 0.455 wt %, about 0.460 wt %, about 0.465 wt %, about 0.470 wt %, about 0.475 wt %, about 0.480 wt %, about 0.485 wt %, about 0.490 wt %, about 0.495 wt %, about 0.500 wt %; or any range encompassed by the foregoing values; or any combination of the foregoing values.

In a further aspect, the disclosed topical formulation comprising therapeutically effective amounts of azelaic acid, minoxidil, finasteride, and duasteride; and one or more compounding agents comprises therapeutically effective amounts of minoxidil, wherein the duasteride is present in an amount of about 0.0005 wt %, about 0.0010 wt %, about 0.0015 wt %, about 0.0020 wt %, about 0.0025 wt %, about 0.0030 wt %, about 0.0035 wt %, about 0.0040 wt %, about 0.0045 wt %, about 0.0050 wt %, about 0.0055 wt %, about 0.0060 wt %, about 0.0065 wt %, about 0.0070 wt %, about 0.0075 wt %, about 0.0080 wt %, about 0.0085 wt %, about 0.0090 wt %, about 0.0095 wt %, about 0.0100 wt %, about 0.0105 wt %, about 0.0110 wt %, about 0.0115 wt %, about 0.0120 wt %, about 0.0125 wt %, about 0.0130 wt %, about 0.0135 wt %, about 0.0140 wt %, about 0.0145 wt %, about 0.0150 wt %, about 0.0155 wt %, about 0.0160 wt %, about 0.0165 wt %, about 0.0170 wt %, about 0.0175 wt %, about 0.0180 wt %, about 0.0185 wt %, about 0.0190 wt %, about 0.0195 wt %, about 0.0200 wt %, about 0.0205 wt %, about 0.0210 wt %, about 0.0215 wt %, about 0.0220 wt %, about 0.0225 wt %, about 0.0230 wt %, about 0.0235 wt %, about 0.0240 wt %, about 0.0245 wt %, about 0.0250 wt %, about 0.0255 wt %, about 0.0260 wt %, about 0.0265 wt %, about 0.0270 wt %, about 0.0275 wt %, about 0.0280 wt %, about 0.0285 wt %, about 0.0290 wt %, about 0.0295 wt %, about 0.0300 wt %; or any range encompassed by the foregoing values; or any combination of the foregoing values.

In various aspects, the present disclosure pertains to topical formulations for treatment of hair loss and/or to increase hair growth, the formulation comprising therapeutically effective amounts of azelaic acid, minoxidil, finasteride, and duasteride; and one or more compounding agents, wherein the one or more compounding agents comprise ethoxy diglycol, propylene glycol, a gel base for gel-cream emulsions, a cream base, a silicone base, or combinations thereof.

In various aspects, the present disclosure pertains to topical formulations for treatment of hair loss and/or to increase hair growth, the formulation comprising azelaic acid, minoxidil, finasteride, and duasteride; and one or more compounding agents, wherein the formulation comprises therapeutically effective amounts of azelaic acid, minoxidil, finasteride, and duasteride; and the one or more compounding agents are present as follows: about 1 vol/wt % to about 10 vol/wt % ethoxy diglycol; about 1 vol/wt % to about 10 vol/wt % propylene glycol; about 5 wt % to about 20 wt % of a gel base for gel-cream emulsions; about 15 wt % to about 35 wt % of a cream base; and about 15 wt % to about 50 wt % of a silicone base; wherein the wt % of a component is based on the total weight of the therapeutic composition and one or more compounding agents; and wherein the vol/wt % of a component is based on the total weight of the therapeutic composition and one or more compounding agents.

In various aspects, the present disclosure pertains to topical formulations for treatment of hair loss and/or to increase hair growth, the formulation comprising azelaic acid, minoxidil, finasteride, and duasteride; and one or more compounding agents wherein the formulation comprises therapeutically effective amounts of azelaic acid, minoxidil, finasteride, and duasteride; and the one or more compounding agents are present as follows: about 4 vol/wt % to about 6 vol/wt % ethoxy diglycol; about 2.5 vol/wt % to about 4.5 vol/wt % propylene glycol; about 8 wt % to about 14 wt % of a gel base for gel-cream emulsions; about 20 wt % to about 30 wt % of a cream base; and about 20 wt % to about 30 wt % of a silicone base; wherein the wt % of a component is based on the total weight of the therapeutic composition and one or more compounding agents; and wherein the vol/wt % of a component is based on the total weight of the therapeutic composition and one or more compounding agents.

In various aspects, the present disclosure pertains to topical formulations for treatment of hair loss and/or to increase hair growth, the formulation comprising azelaic acid, minoxidil, finasteride, and duasteride; and one or more compounding agents; wherein formulation comprising: a therapeutic composition comprising therapeutically effective amounts of azelaic acid, minoxidil, finasteride, and duasteride; and wherein the one or more compounding agents are present as follows: about 6 vol/wt % ethoxy diglycol; about 3.5 vol/wt % propylene glycol; about 11 wt % of a gel base for gel-cream emulsions; about 21 wt % to about 23 wt % of a cream base; and about 26 wt % to about 29 wt % of a silicone base; wherein the wt % of a component is based on the total weight of the therapeutic composition and one or more compounding agents; and wherein the vol/wt % of a component is based on the total weight of the therapeutic composition and one or more compounding agents.

In a further aspect, the disclosed topical formulation the present disclosure pertains to topical formulations for treatment of hair loss and/or to increase hair growth, the formulation comprising azelaic acid, minoxidil, finasteride, and duasteride; and one or more compounding agents; wherein formulation comprises therapeutically effective amounts of azelaic acid, minoxidil, finasteride, and duasteride; and wherein the formulation comprises ethoxy glycol in an amount of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising azelaic acid, minoxidil, finasteride, and duasteride; and one or more compounding agents; wherein formulation comprises therapeutically effective amounts of azelaic acid, minoxidil, finasteride, and duasteride; and wherein the formulation comprises propylene glycol in an amount of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising azelaic acid, minoxidil, finasteride, and duasteride; and one or more compounding agents; wherein formulation comprises therapeutically effective amounts of azelaic acid, minoxidil, finasteride, and duasteride; and wherein the formulation comprises a gel base for gel-cream emulsions in an amount of about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %, about 10.1 wt %, about 10.2 wt %, about 10.3 wt %, about 10.4 wt %, about 10.5 wt %, about 10.6 wt %, about 10.7 wt %, about 10.8 wt %, about 10.9 wt %, about 11.0 wt %, about 11.1 wt %, about 11.2 wt %, about 11.3 wt %, about 11.4 wt %, about 11.5 wt %, about 11.6 wt %, about 11.7 wt %, about 11.8 wt %, about 11.9 wt %, about 12.0 wt %, about 12.1 wt %, about 12.2 wt %, about 12.3 wt %, about 12.4 wt %, about 12.5 wt %, about 12.6 wt %, about 12.7 wt %, about 12.8 wt %, about 12.9 wt %, about 13.0 wt %, about 13.1 wt %, about 13.2 wt %, about 13.3 wt %, about 13.4 wt %, about 13.5 wt %, about 13.6 wt %, about 13.7 wt %, about 13.8 wt %, about 13.9 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising azelaic acid, minoxidil, finasteride, and duasteride; and one or more compounding agents; wherein formulation comprises therapeutically effective amounts of azelaic acid, minoxidil, finasteride, and duasteride; and wherein the formulation comprises a cream base in an amount of about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %, about 20.1 wt %, about 20.2 wt %, about 20.3 wt %, about 20.4 wt %, about 20.5 wt %, about 20.6 wt %, about 20.7 wt %, about 20.8 wt %, about 20.9 wt %, about 21.0 wt %, about 21.1 wt %, about 21.2 wt %, about 21.3 wt %, about 21.4 wt %, about 21.5 wt %, about 21.6 wt %, about 21.7 wt %, about 21.8 wt %, about 21.9 wt %, about 22.0 wt %, about 22.1 wt %, about 22.2 wt %, about 22.3 wt %, about 22.4 wt %, about 22.5 wt %, about 22.6 wt %, about 22.7 wt %, about 22.8 wt %, about 22.9 wt %, about 23.0 wt %, about 23.1 wt %, about 23.2 wt %, about 23.3 wt %, about 23.4 wt %, about 23.5 wt %, about 23.6 wt %, about 23.7 wt %, about 23.8 wt %, about 23.9 wt %, about 24.0 wt %, about 24.1 wt %, about 24.2 wt %, about 24.3 wt %, about 24.4 wt %, about 24.5 wt %, about 24.6 wt %, about 24.7 wt %, about 24.8 wt %, about 24.9 wt %, about 25.0 wt %, about 25.1 wt %, about 25.2 wt %, about 25.3 wt %, about 25.4 wt %, about 25.5 wt %, about 25.6 wt %, about 25.7 wt %, about 25.8 wt %, about 25.9 wt %, about 26.0 wt %, about 26.1 wt %, about 26.2 wt %, about 26.3 wt %, about 26.4 wt %, about 26.5 wt %, about 26.6 wt %, about 26.7 wt %, about 26.8 wt %, about 26.9 wt %, about 27.0 wt %, about 27.1 wt %, about 27.2 wt %, about 27.3 wt %, about 27.4 wt %, about 27.5 wt %, about 27.6 wt %, about 27.7 wt %, about 27.8 wt %, about 27.9 wt %, about 28.0 wt %, about 28.1 wt %, about 28.2 wt %, about 28.3 wt %, about 28.4 wt %, about 28.5 wt %, about 28.6 wt %, about 28.7 wt %, about 28.8 wt %, about 28.9 wt %, about 29.0 wt %, about 29.1 wt %, about 29.2 wt %, about 29.3 wt %, about 29.4 wt %, about 29.5 wt %, about 29.6 wt %, about 29.7 wt %, about 29.8 wt %, about 29.9 wt %, about 30.0 wt %, about 30.1 wt %, about 30.2 wt %, about 30.3 wt %, about 30.4 wt %, about 30.5 wt %, about 30.6 wt %, about 30.7 wt %, about 30.8 wt %, about 30.9 wt %, about 31.0 wt %, about 31.1 wt %, about 31.2 wt %, about 31.3 wt %, about 31.4 wt %, about 31.5 wt %, about 31.6 wt %, about 31.7 wt %, about 31.8 wt %, about 31.9 wt %, about 32.0 wt %, about 32.1 wt %, about 32.2 wt %, about 32.3 wt %, about 32.4 wt %, about 32.5 wt %, about 32.6 wt %, about 32.7 wt %, about 32.8 wt %, about 32.9 wt %, about 33.0 wt %, about 33.1 wt %, about 33.2 wt %, about 33.3 wt %, about 33.4 wt %, about 33.5 wt %, about 33.6 wt %, about 33.7 wt %, about 33.8 wt %, about 33.9 wt %, about 34.0 wt %, about 34.1 wt %, about 34.2 wt %, about 34.3 wt %, about 34.4 wt %, about 34.5 wt %, about 34.6 wt %, about 34.7 wt %, about 34.8 wt %, about 34.9 wt %, about 35.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising azelaic acid, minoxidil, finasteride, and duasteride; and one or more compounding agents; wherein formulation comprises therapeutically effective amounts of azelaic acid, minoxidil, finasteride, and duasteride; and wherein the formulation comprises a silicone base in an amount of about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %, about 20.1 wt %, about 20.2 wt %, about 20.3 wt %, about 20.4 wt %, about 20.5 wt %, about 20.6 wt %, about 20.7 wt %, about 20.8 wt %, about 20.9 wt %, about 21.0 wt %, about 21.1 wt %, about 21.2 wt %, about 21.3 wt %, about 21.4 wt %, about 21.5 wt %, about 21.6 wt %, about 21.7 wt %, about 21.8 wt %, about 21.9 wt %, about 22.0 wt %, about 22.1 wt %, about 22.2 wt %, about 22.3 wt %, about 22.4 wt %, about 22.5 wt %, about 22.6 wt %, about 22.7 wt %, about 22.8 wt %, about 22.9 wt %, about 23.0 wt %, about 23.1 wt %, about 23.2 wt %, about 23.3 wt %, about 23.4 wt %, about 23.5 wt %, about 23.6 wt %, about 23.7 wt %, about 23.8 wt %, about 23.9 wt %, about 24.0 wt %, about 24.1 wt %, about 24.2 wt %, about 24.3 wt %, about 24.4 wt %, about 24.5 wt %, about 24.6 wt %, about 24.7 wt %, about 24.8 wt %, about 24.9 wt %, about 25.0 wt %, about 25.1 wt %, about 25.2 wt %, about 25.3 wt %, about 25.4 wt %, about 25.5 wt %, about 25.6 wt %, about 25.7 wt %, about 25.8 wt %, about 25.9 wt %, about 26.0 wt %, about 26.1 wt %, about 26.2 wt %, about 26.3 wt %, about 26.4 wt %, about 26.5 wt %, about 26.6 wt %, about 26.7 wt %, about 26.8 wt %, about 26.9 wt %, about 27.0 wt %, about 27.1 wt %, about 27.2 wt %, about 27.3 wt %, about 27.4 wt %, about 27.5 wt %, about 27.6 wt %, about 27.7 wt %, about 27.8 wt %, about 27.9 wt %, about 28.0 wt %, about 28.1 wt %, about 28.2 wt %, about 28.3 wt %, about 28.4 wt %, about 28.5 wt %, about 28.6 wt %, about 28.7 wt %, about 28.8 wt %, about 28.9 wt %, about 29.0 wt %, about 29.1 wt %, about 29.2 wt %, about 29.3 wt %, about 29.4 wt %, about 29.5 wt %, about 29.6 wt %, about 29.7 wt %, about 29.8 wt %, about 29.9 wt %, about 30.0 wt %, about 30.1 wt %, about 30.2 wt %, about 30.3 wt %, about 30.4 wt %, about 30.5 wt %, about 30.6 wt %, about 30.7 wt %, about 30.8 wt %, about 30.9 wt %, about 31.0 wt %, about 31.1 wt %, about 31.2 wt %, about 31.3 wt %, about 31.4 wt %, about 31.5 wt %, about 31.6 wt %, about 31.7 wt %, about 31.8 wt %, about 31.9 wt %, about 32.0 wt %, about 32.1 wt %, about 32.2 wt %, about 32.3 wt %, about 32.4 wt %, about 32.5 wt %, about 32.6 wt %, about 32.7 wt %, about 32.8 wt %, about 32.9 wt %, about 33.0 wt %, about 33.1 wt %, about 33.2 wt %, about 33.3 wt %, about 33.4 wt %, about 33.5 wt %, about 33.6 wt %, about 33.7 wt %, about 33.8 wt %, about 33.9 wt %, about 34.0 wt %, about 34.1 wt %, about 34.2 wt %, about 34.3 wt %, about 34.4 wt %, about 34.5 wt %, about 34.6 wt %, about 34.7 wt %, about 34.8 wt %, about 34.9 wt %, about 35.0 wt %, about 35.1 wt %, about 35.2 wt %, about 35.3 wt %, about 35.4 wt %, about 35.5 wt %, about 35.6 wt %, about 35.7 wt %, about 35.8 wt %, about 35.9 wt %, about 36.0 wt %, about 36.1 wt %, about 36.2 wt %, about 36.3 wt %, about 36.4 wt %, about 36.5 wt %, about 36.6 wt %, about 36.7 wt %, about 36.8 wt %, about 36.9 wt %, about 37.0 wt %, about 37.1 wt %, about 37.2 wt %, about 37.3 wt %, about 37.4 wt %, about 37.5 wt %, about 37.6 wt %, about 37.7 wt %, about 37.8 wt %, about 37.9 wt %, about 38.0 wt %, about 38.1 wt %, about 38.2 wt %, about 38.3 wt %, about 38.4 wt %, about 38.5 wt %, about 38.6 wt %, about 38.7 wt %, about 38.8 wt %, about 38.9 wt %, about 39.0 wt %, about 39.1 wt %, about 39.2 wt %, about 39.3 wt %, about 39.4 wt %, about 39.5 wt %, about 39.6 wt %, about 39.7 wt %, about 39.8 wt %, about 39.9 wt %, about 40.0 wt %, about 40.1 wt %, about 40.2 wt %, about 40.3 wt %, about 40.4 wt %, about 40.5 wt %, about 40.6 wt %, about 40.7 wt %, about 40.8 wt %, about 40.9 wt %, about 41.0 wt %, about 41.1 wt %, about 41.2 wt %, about 41.3 wt %, about 41.4 wt %, about 41.5 wt %, about 41.6 wt %, about 41.7 wt %, about 41.8 wt %, about 41.9 wt %, about 42.0 wt %, about 42.1 wt %, about 42.2 wt %, about 42.3 wt %, about 42.4 wt %, about 42.5 wt %, about 42.6 wt %, about 42.7 wt %, about 42.8 wt %, about 42.9 wt %, about 43.0 wt %, about 43.1 wt %, about 43.2 wt %, about 43.3 wt %, about 43.4 wt %, about 43.5 wt %, about 43.6 wt %, about 43.7 wt %, about 43.8 wt %, about 43.9 wt %, about 44.0 wt %, about 44.1 wt %, about 44.2 wt %, about 44.3 wt %, about 44.4 wt %, about 44.5 wt %, about 44.6 wt %, about 44.7 wt %, about 44.8 wt %, about 44.9 wt %, about 45.0 wt %, about 45.1 wt %, about 45.2 wt %, about 45.3 wt %, about 45.4 wt %, about 45.5 wt %, about 45.6 wt %, about 45.7 wt %, about 45.8 wt %, about 45.9 wt %, about 46.0 wt %, about 46.1 wt %, about 46.2 wt %, about 46.3 wt %, about 46.4 wt %, about 46.5 wt %, about 46.6 wt %, about 46.7 wt %, about 46.8 wt %, about 46.9 wt %, about 47.0 wt %, about 47.1 wt %, about 47.2 wt %, about 47.3 wt %, about 47.4 wt %, about 47.5 wt %, about 47.6 wt %, about 47.7 wt %, about 47.8 wt %, about 47.9 wt %, about 48.0 wt %, about 48.1 wt %, about 48.2 wt %, about 48.3 wt %, about 48.4 wt %, about 48.5 wt %, about 48.6 wt %, about 48.7 wt %, about 48.8 wt %, about 48.9 wt %, about 49.0 wt %, about 49.1 wt %, about 49.2 wt %, about 49.3 wt %, about 49.4 wt %, about 49.5 wt %, about 49.6 wt %, about 49.7 wt %, about 49.8 wt %, about 49.9 wt %, about 50.0 wt %; or any range encompassed by the foregoing values; or any combination of the foregoing values.

In various aspects, the ethoxy diglycol used in the disclosed formulations has a specific gravity of about 0.9 to about 1.10. In a further aspect, the ethoxy diglycol used in the disclosed formulations has a specific gravity of about 1.02 to about 1.07. Without wishing to be bound by a particular theory, it is believed that the ethoxy diglycol can act as a carrier for the various ingredients, including active ingredients, and/or as a skin penetrant.

In various aspects, the propylene glycol used in the disclosed formulations has a specific gravity of about 0.9 to about 1.3. In a further aspect, the propylene glycol used in the disclosed formulations has a specific gravity of about 1.05 to about 1.15. Without wishing to be bound by a particular theory, it is believed that the propylene glycol can as a viscosity control agent. That is, the amount of propylene glycol used can be adjust to achieve a desired viscosity in the disclosed formulation.

In a further aspect, the gel base for gel-cream emulsions used in the disclosed formulations comprises water and one or more of the following: ammonium acryloyldimethyltaurate copolymer, aloe barbadensis leaf juice powder, allatoin, disodium EDTA, methylchloroisothiazolinone, or methylisothiazolinone. In a still further aspect, the gel base for gel-cream emulsions used in the disclosed formulations comprises water and one or more of the following: a high molecular weight silicone elastomer gel, including, but not limited to, PEG-12 dimethicone/PPG-20 crosspolymer; *Butyrospermum parkii* (shea butter); a cross-linked siloxane, including, but not limited to, polysilicone-11; tocopheryl acetate; or BHT. In a yet further aspect, the gel base for gel-cream emulsions used in the disclosed formulations comprises water and one or more of the following: ammonium acryloyldimethyltaurate copolymer, aloe barbadensis leaf juice powder, allatoin, disodium EDTA, methylchloroisothiazolinone, methylisothiazolinone; a dimethicone, including, but not limited to caprylyl methicone; a high molecular weight silicone elastomer gel, including, but not limited to, PEG-12 dimethicone/PPG-20 crosspolymer; *Butyrospermum parkii* (shea butter); a cross-linked siloxane, including, but not limited to, polysilicone-11; tocopheryl acetate; or BHT.

In various aspects, the silicone base used in the disclosed formulations comprise one or more of the following: cyclopentasiloxane, polysilicone-11, C30-45 alkyl cetearyl dimethicone crosspolymer, dimethiconol, phenyl trimethicone, or PEG PPG dimethicone. In a further aspect, the silicone base used in the disclosed formulations comprise one or more of the following: cyclopetasiloxane, polysilicone-11, laureth-4, macadamia seed oil, glycereth-8 esters, phenyl trimethicone, C30-45 alkyl ceteryl dimethicone crossploymer, dimethiconol, PEG PPG dimethicone, PEG-30 dipolyhydroxysterate, *Carapa guaianensis* seed oil, or Pracaxi Oil, e.g., an oil derived from the seeds of the *Pentaclethra macroloba* tree. In a still further aspect, the silicone base used in the disclosed formulations comprise one or more of the following: cyclopentasiloxane, polysilicone-11, C30-45 alkyl cetearyl dimethicone crosspolymer, dimethiconol, phenyl trimethicone, PEG PPG dimethicone, cyclopetasiloxane, polysilicone-11, laureth-4, macadamia seed oil, glycereth-8 esters, phenyl trimethicone, C30-45 alkyl ceteryl dimethicone crossploymer, dimethiconol, PEG PPG dimethicone, PEG-30 dipolyhydroxysterate, *Carapa guaianensis* seed oil, or Pracaxi Oil, e.g., an oil derived from the seeds of the *Pentaclethra macroloba* tree.

In a further aspect, the silicone base used in the disclosed formulations further comprises a one or more fatty acids. In a still further aspect. In various aspects, the silicone base used in the disclosed formulations further comprises an *Carapa guaianensis* seed oil, macadamia nut oil, laureth-4, PEG 30 dipolyhydroxystearate, or combinations thereof.

In various aspects, the silicone base used in the disclosed formulations has a pH of about 5.5 to about 6.5. In a further aspect, the silicone base used in the disclosed formulations has a pH of about 5.9 to about 6.1.

In various aspects, the silicone base used in the disclosed formulations has a specific gravity of about 0.90 to about 1.30. In a further aspect, the silicon base used in the disclosed formulations has a specific gravity of about 1.07 to about 1.20.

In various aspects, the cream base used in the disclosed formulations comprise one or more of the following: purified water, white petrolatum, cetyl alcohol, steryl alcohol, propylene glycol, glyerin, sodium lauryl sulfate, diazolidinyl urea, iodopropynyl butylcarbamate, laureth-23, *Glycine soja* oil (e.g., a soybean oil derived from the *Glycine soja* plant), one or more fatty acids, e.g., oleic acid, paraffinum liquuidium, lanolin, laneth-16, triethanolamine, tocopheral acetate, retinyl palmitate, or *Aloe barbadenis* leaf powder.

In various aspects, the disclosed formulations can further comprise caffeine, saw palmetto extract, or a combination thereof. Without wishing to be bound by a particular theory, it is believed that caffeine can have a beneficial effect in the disclosed formulation, e.g., increasing blood flow in the area to which the disclosed formulation is applied. Similarly, without wishing to be bound by a particular theory, it is believed that saw palmetto extract can have a beneficial effect in the disclosed formulation, e.g., increasing blood flow in the area to which the disclosed formulation is applied.

In a further aspect, the disclosed formulations can further comprise caffeine present in an amount from about 0.0001 wt % to about 0.007 wt %. In a further aspect, the disclosed formulations can further comprise caffeine present in an amount of about 0.00010 wt %, about 0.00015 wt %, about 0.00020 wt %, about 0.0025 wt %, about 0.00030 wt %, about 0.00035 wt %, about 0.00040 wt %, about 0.00045 wt %, about 0.00050 wt %, about 0.00055 wt %, about 0.00060 wt %, about 0.00065 wt %, about 0.00070 wt %, about 0.00075 wt %, about 0.00080 wt %, about 0.00085 wt %, about 0.00090 wt %, about 0.00095 wt %, about 0.00100 wt %, about 0.00105 wt %, about 0.00110 wt %, about 0.00115 wt %, about 0.00120 wt %, about 0.00125 wt %, about 0.00130 wt %, about 0.00135 wt %, about 0.00140 wt %, about 0.00145 wt %, about 0.00150 wt %, about 0.00155 wt %, about 0.00160 wt %, about 0.00165 wt %, about 0.00170 wt %, about 0.00175 wt %, about 0.00180 wt %, about 0.00185 wt %, about 0.00190 wt %, about 0.00195 wt %, about 0.0020 wt %, about 0.0025 wt %, about 0.0030 wt %, about 0.0035 wt %, about 0.0040 wt %, about 0.0045 wt %, about 0.0050 wt %, about 0.0055 wt %, about 0.0060 wt %, about 0.0065 wt %, about 0.0070 wt %; or any range encompassed by the foregoing values; or any combination of the foregoing values.

In a further aspect, the disclosed formulations can further comprise saw palmetto extract present in an amount from about 0.1 wt % to about 15 wt %. In a further aspect, the disclosed formulations can further comprise saw palmetto extract present in an amount of about 0.10 wt %, about 0.20 wt %, about 0.30 wt %, about 0.40 wt %, about 0.50 wt %, about 0.60 wt %, about 0.70 wt %, about 0.80 wt %, about 0.90 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %, about 10.1 wt %, about 10.2 wt %, about 10.3 wt %, about 10.4 wt %, about 10.5 wt %, about 10.6 wt %, about 10.7 wt %, about 10.8 wt %, about 10.9 wt %, about 11.0 wt %, about 11.1 wt %, about 11.2 wt %, about 11.3 wt %, about 11.4 wt %, about 11.5 wt %, about 11.6 wt %, about 11.7 wt %, about 11.8 wt %, about 11.9 wt %, about 12.0 wt %, about 12.1 wt %, about 12.2 wt %, about 12.3 wt %, about 12.4 wt %, about 12.5 wt %, about 12.6 wt %, about 12.7 wt %, about 12.8 wt %, about 12.9 wt %, about 13.0 wt %, about 13.1 wt %, about 13.2 wt %, about 13.3 wt %, about 13.4 wt %, about 13.5 wt %, about 13.6 wt %, about 13.7 wt %, about 13.8 wt %, about 13.9 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %; or any range encompassed by the foregoing values; or any combination of the foregoing values.

In a further aspect, the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract.

In a further aspect, the disclosed topical formulation comprising therapeutically effective amounts of azelaic acid, minoxidil, finasteride, and duasteride; one or more compounding agents; and optionally caffeine and/or saw palmetto extract; wherein the formulation comprises therapeutically effective amounts of azelaic acid, minoxidil, finasteride, and duasteride as follows: about 0.100 wt % to about 0.500 wt % azelaic acid; about 10 wt % to about 20 wt % minoxidil; about 0.05 wt % to about 0.50 wt % finasteride; and about 0.001 wt % to about 0.030 wt % duasteride; wherein the wt % of a component is based on the total weight of the therapeutic composition; and one or more compound agents.

In a further aspect, the disclosed topical formulation comprising therapeutically effective amounts of azelaic acid, minoxidil, finasteride, and duasteride; one or more compounding agents; and optionally caffeine and/or saw palmetto extract; wherein the formulation comprises therapeutically effective amounts of azelaic acid, minoxidil, finasteride, and duasteride as follows: about 0.300 wt % to about 0.400 wt % azelaic acid; about 12 wt % to about 17 wt % minoxidil; about 0.10 wt % to about 0.30 wt % finasteride; and about 0.005 wt % to about 0.015 wt % duasteride; wherein the wt % of a component is based on the total weight of the therapeutic composition; and one or more compounding agents.

In a further aspect, the disclosed topical formulation comprising therapeutically effective amounts of azelaic acid, minoxidil, finasteride, and duasteride; one or more compounding agents; and optionally caffeine and/or saw palmetto extract; wherein the formulation comprises therapeutically effective amounts of azelaic acid, minoxidil, finasteride, and duasteride as follows: about 0.325 wt % azelaic acid; about 15 wt % minoxidil; about 0.20 wt % finasteride; and about 0.010 wt % duasteride; wherein the wt % of a component is based on the total weight of the therapeutic composition and one or more compounding agents.

In a further aspect, the disclosed topical formulation comprising therapeutically effective amounts of azelaic acid, minoxidil, finasteride, and duasteride; one or more compounding agents; and optionally caffeine and/or saw palmetto extract; wherein the azelaic acid is present in an amount of about 0.100 wt %, about 0.105 wt %, about 0.110 wt %, about 0.115 wt %, about 0.120 wt %, about 0.125 wt %, about 0.130 wt %, about 0.135 wt %, about 0.140 wt %, about 0.145 wt %, about 0.150 wt %, about 0.155 wt %, about 0.160 wt %, about 0.165 wt %, about 0.170 wt %, about 0.175 wt %, about 0.180 wt %, about 0.185 wt %, about 0.190 wt %, about 0.195 wt %, about 0.200 wt %, about 0.205 wt %, about 0.210 wt %, about 0.215 wt %, about 0.220 wt %, about 0.225 wt %, about 0.230 wt %, about 0.235 wt %, about 0.240 wt %, about 0.245 wt %, about 0.250 wt %, about 0.255 wt %, about 0.260 wt %, about 0.265 wt %, about 0.270 wt %, about 0.275 wt %, about 0.280 wt %, about 0.285 wt %, about 0.290 wt %, about 0.295 wt %, about 0.300 wt %, about 0.305 wt %, about 0.310 wt %, about 0.315 wt %, about 0.320 wt %, about 0.325 wt %, about 0.330 wt %, about 0.335 wt %, about 0.340 wt %, about 0.345 wt %, about 0.350 wt %, about 0.355 wt %, about 0.360 wt %, about 0.365 wt %, about 0.370 wt %, about 0.375 wt %, about 0.380 wt %, about 0.385 wt %, about 0.390 wt %, about 0.395 wt %, about 0.400 wt %, about 0.405 wt %, about 0.410 wt %, about 0.415 wt %, about 0.420 wt %, about 0.425 wt %, about 0.430 wt %, about 0.435 wt %, about 0.440 wt %, about 0.445 wt %, about 0.450 wt %, about 0.455 wt %, about 0.460 wt %, about 0.465 wt %, about 0.470 wt %, about 0.475 wt %, about 0.480 wt %, about 0.485 wt %, about 0.490 wt %, about 0.495 wt %, about 0.500 wt %; or any range encompassed by the foregoing values; or any combination of the foregoing values.

In a further aspect, the disclosed topical formulation comprising therapeutically effective amounts of azelaic acid, minoxidil, finasteride, and duasteride; one or more compounding agents; and optionally caffeine and/or saw palmetto extract; wherein the minoxidil is present in an amount of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %, about 10.1 wt %, about 10.2 wt %, about 10.3 wt %, about 10.4 wt %, about 10.5 wt %, about 10.6 wt %, about 10.7 wt %, about 10.8 wt %, about 10.9 wt %, about 11.0 wt %, about 11.1 wt %, about 11.2 wt %, about 11.3 wt %, about 11.4 wt %, about 11.5 wt %, about 11.6 wt %, about 11.7 wt %, about 11.8 wt %, about 11.9 wt %, about 12.0 wt %, about 12.1 wt %, about 12.2 wt %, about 12.3 wt %, about 12.4 wt %, about 12.5 wt %, about 12.6 wt %, about 12.7 wt %, about 12.8 wt %, about 12.9 wt %, about 13.0 wt %, about 13.1 wt %, about 13.2 wt %, about 13.3 wt %, about 13.4 wt %, about 13.5 wt %, about 13.6 wt %, about 13.7 wt %, about 13.8 wt %, about 13.9 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %; or any range encompassed by the foregoing values; or any combination of the foregoing values.

In a further aspect, the disclosed topical formulation comprising therapeutically effective amounts of azelaic acid, minoxidil, finasteride, and duasteride; one or more compounding agents; and optionally caffeine and/or saw palmetto extract; wherein the finasteride is present in an amount of about 0.010 wt %, about 0.015 wt %, about 0.020 wt %, about 0.025 wt %, about 0.030 wt %, about 0.035 wt %, about 0.040 wt %, about 0.045 wt %, about 0.050 wt %, about 0.055 wt %, about 0.060 wt %, about 0.065 wt %, about 0.070 wt %, about 0.075 wt %, about 0.080 wt %, about 0.085 wt %, about 0.090 wt %, about 0.095 wt %, about 0.100 wt %, about 0.105 wt %, about 0.110 wt %, about 0.115 wt %, about 0.120 wt %, about 0.125 wt %, about 0.130 wt %, about 0.135 wt %, about 0.140 wt %, about 0.145 wt %, about 0.150 wt %, about 0.155 wt %, about 0.160 wt %, about 0.165 wt %, about 0.170 wt %, about 0.175 wt %, about 0.180 wt %, about 0.185 wt %, about 0.190 wt %, about 0.195 wt %, about 0.200 wt %, about 0.205 wt %, about 0.210 wt %, about 0.215 wt %, about 0.220 wt %, about 0.225 wt %, about 0.230 wt %, about 0.235 wt %, about 0.240 wt %, about 0.245 wt %, about 0.250 wt %, about 0.255 wt %, about 0.260 wt %, about 0.265 wt %, about 0.270 wt %, about 0.275 wt %, about 0.280 wt %, about 0.285 wt %, about 0.290 wt %, about 0.295 wt %, about 0.300 wt %, about 0.305 wt %, about 0.310 wt %, about 0.315 wt %, about 0.320 wt %, about 0.325 wt %, about 0.330 wt %, about 0.335 wt %, about 0.340 wt %, about 0.345 wt %, about 0.350 wt %, about 0.355 wt %, about 0.360 wt %, about 0.365 wt %, about 0.370 wt %, about 0.375 wt %, about 0.380 wt %, about 0.385 wt %, about 0.390 wt %, about 0.395 wt %, about 0.400 wt %, about 0.405 wt %, about 0.410 wt %, about 0.415 wt %, about 0.420 wt %, about 0.425 wt %, about 0.430 wt %, about 0.435 wt %, about 0.440 wt %, about 0.445 wt %, about 0.450 wt %, about 0.455 wt %, about 0.460 wt %, about 0.465 wt %, about 0.470 wt %, about 0.475 wt %, about 0.480 wt %, about 0.485 wt %, about 0.490 wt %, about 0.495 wt %, about 0.500 wt %; or any range encompassed by the foregoing values; or any combination of the foregoing values.

In a further aspect, the disclosed topical formulation comprising therapeutically effective amounts of azelaic acid, minoxidil, finasteride, and duasteride; one or more compounding agents; and optionally caffeine and/or saw palmetto extract; wherein the duasteride is present in an amount of about 0.0005 wt %, about 0.0010 wt %, about 0.0015 wt %, about 0.0020 wt %, about 0.0025 wt %, about 0.0030 wt %, about 0.0035 wt %, about 0.0040 wt %, about 0.0045 wt %, about 0.0050 wt %, about 0.0055 wt %, about 0.0060 wt %, about 0.0065 wt %, about 0.0070 wt %, about 0.0075 wt %, about 0.0080 wt %, about 0.0085 wt %, about 0.0090 wt %, about 0.0095 wt %, about 0.0100 wt %, about 0.0105 wt %, about 0.0110 wt %, about 0.0115 wt %, about 0.0120 wt %, about 0.0125 wt %, about 0.0130 wt %, about 0.0135 wt %, about 0.0140 wt %, about 0.0145 wt %, about 0.0150 wt %, about 0.0155 wt %, about 0.0160 wt %, about 0.0165 wt %, about 0.0170 wt %, about 0.0175 wt %, about 0.0180 wt %, about 0.0185 wt %, about 0.0190 wt %, about 0.0195 wt %, about 0.0200 wt %, about 0.0205 wt %, about 0.0210 wt %, about 0.0215 wt %, about 0.0220 wt %, about 0.0225 wt %, about 0.0230 wt %, about 0.0235 wt %, about 0.0240 wt %, about 0.0245 wt %, about 0.0250 wt %, about 0.0255 wt %, about 0.0260 wt %, about 0.0265 wt %, about 0.0270 wt %, about 0.0275 wt %, about 0.0280 wt %, about 0.0285 wt %, about 0.0290 wt %, about 0.0295 wt %, about 0.0300 wt %; or any range encompassed by the foregoing values; or any combination of the foregoing values.

In various aspects, the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract; wherein the one or more compounding agents comprise ethoxy diglycol, propylene glycol, a gel base for gel-cream emulsions, a cream base, a silicone base, or combinations thereof.

In various aspects, the present disclosure pertains to topical formulations for treatment of hair loss and/or to increase hair growth, the formulation comprising: a therapeutic composition comprising therapeutically effective amounts of azelaic acid, minoxidil, finasteride, duasteride; one or more compounding agents; and optionally caffeine and/or saw palmetto extract; wherein formulation comprises a therapeutically effective amount of azelaic acid, minoxidil, finasteride, and duasteride; and the one or more compounding agents are present as follows: about 1 vol/wt % to about 10 vol/wt % ethoxy diglycol; about 1 vol/wt % to about 10 vol/wt % propylene glycol; about 5 wt % to about 20 wt % of a gel base for gel-cream emulsions; about 15 wt % to about 35 wt % of a cream base; and about 15 wt % to about 50 wt % of a silicone base; wherein the wt % of a component is based on the total weight of the therapeutic composition and one or more compounding agents; and wherein the vol/wt % of a component is based on the total weight of the therapeutic composition and one or more compounding agents.

In various aspects, the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract; wherein formulation comprises a therapeutically effective amount of azelaic acid, minoxidil, finasteride, and duasteride; and the one or more compounding agents are present as follows: about 4 vol/wt % to about 6 vol/wt % ethoxy diglycol; about 2.5 vol/wt % to about 4.5 vol/wt % propylene glycol; about 8 wt % to about 14 wt % of a gel base for gel-cream emulsions; about 20 wt % to about 30 wt % of a cream base; and about 20 wt % to about 30 wt % of a silicone base; wherein the wt % of a component is based on the total weight of the therapeutic composition and one or more compounding agents; and wherein the vol/wt % of a component is based on the total weight of the therapeutic composition and one or more compounding agents.

In various aspects, the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract; wherein formulation comprises a therapeutically effective amount of azelaic acid, minoxidil, finasteride, and duasteride; and the one or more compounding agents are present as follows: about 6 vol/wt % ethoxy diglycol; about 3.5 vol/wt % propylene glycol; about 11 wt % of a gel base for gel-cream emulsions; about 21 wt % to about 23 wt % of a cream base; and about 26 wt % to about 29 wt % of a silicone base; wherein the wt % of a component is based on the total weight of the therapeutic composition and one or more compounding agents; and wherein the vol/wt % of a component is based on the total weight of the therapeutic composition and one or more compounding agents.

In a further aspect, the disclosed topical formulation the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract; wherein formulation comprises a therapeutically effective amount of azelaic acid, minoxidil, finasteride, and duasteride; and the formulation comprises ethoxy glycol in an amount of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract; wherein formulation comprises a therapeutically effective amount of azelaic acid, minoxidil, finasteride, and duasteride; and the formulation comprises propylene glycol in an amount of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract; wherein formulation comprises a therapeutically effective amount of azelaic acid, minoxidil, finasteride, and duasteride; and the formulation comprises a gel base for gel-cream emulsions in an amount of about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %, about 10.1 wt %, about 10.2 wt %, about 10.3 wt %, about 10.4 wt %, about 10.5 wt %, about 10.6 wt %, about 10.7 wt %, about 10.8 wt %, about 10.9 wt %, about 11.0 wt %, about 11.1 wt %, about 11.2 wt %, about 11.3 wt %, about 11.4 wt %, about 11.5 wt %, about 11.6 wt %, about 11.7 wt %, about 11.8 wt %, about 11.9 wt %, about 12.0 wt %, about 12.1 wt %, about 12.2 wt %, about 12.3 wt %, about 12.4 wt %, about 12.5 wt %, about 12.6 wt %, about 12.7 wt %, about 12.8 wt %, about 12.9 wt %, about 13.0 wt %, about 13.1 wt %, about 13.2 wt %, about 13.3 wt %, about 13.4 wt %, about 13.5 wt %, about 13.6 wt %, about 13.7 wt %, about 13.8 wt %, about 13.9 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract; wherein formulation comprises a therapeutically effective amount of azelaic acid, minoxidil, finasteride, and duasteride; and the formulation comprises a cream base in an amount of about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %, about 20.1 wt %, about 20.2 wt %, about 20.3 wt %, about 20.4 wt %, about 20.5 wt %, about 20.6 wt %, about 20.7 wt %, about 20.8 wt %, about 20.9 wt %, about 21.0 wt %, about 21.1 wt %, about 21.2 wt %, about 21.3 wt %, about 21.4 wt %, about 21.5 wt %, about 21.6 wt %, about 21.7 wt %, about 21.8 wt %, about 21.9 wt %, about 22.0 wt %, about 22.1 wt %, about 22.2 wt %, about 22.3 wt %, about 22.4 wt %, about 22.5 wt %, about 22.6 wt %, about 22.7 wt %, about 22.8 wt %, about 22.9 wt %, about 23.0 wt %, about 23.1 wt %, about 23.2 wt %, about 23.3 wt %, about 23.4 wt %, about 23.5 wt %, about 23.6 wt %, about 23.7 wt %, about 23.8 wt %, about 23.9 wt %, about 24.0 wt %, about 24.1 wt %, about 24.2 wt %, about 24.3 wt %, about 24.4 wt %, about 24.5 wt %, about 24.6 wt %, about 24.7 wt %, about 24.8 wt %, about 24.9 wt %, about 25.0 wt %, about 25.1 wt %, about 25.2 wt %, about 25.3 wt %, about 25.4 wt %, about 25.5 wt %, about 25.6 wt %, about 25.7 wt %, about 25.8 wt %, about 25.9 wt %, about 26.0 wt %, about 26.1 wt %, about 26.2 wt %, about 26.3 wt %, about 26.4 wt %, about 26.5 wt %, about 26.6 wt %, about 26.7 wt %, about 26.8 wt %, about 26.9 wt %, about 27.0 wt %, about 27.1 wt %, about 27.2 wt %, about 27.3 wt %, about 27.4 wt %, about 27.5 wt %, about 27.6 wt %, about 27.7 wt %, about 27.8 wt %, about 27.9 wt %, about 28.0 wt %, about 28.1 wt %, about 28.2 wt %, about 28.3 wt %, about 28.4 wt %, about 28.5 wt %, about 28.6 wt %, about 28.7 wt %, about 28.8 wt %, about 28.9 wt %, about 29.0 wt %, about 29.1 wt %, about 29.2 wt %, about 29.3 wt %, about 29.4 wt %, about 29.5 wt %, about 29.6 wt %, about 29.7 wt %, about 29.8 wt %, about 29.9 wt %, about 30.0 wt %, about 30.1 wt %, about 30.2 wt %, about 30.3 wt %, about 30.4 wt %, about 30.5 wt %, about 30.6 wt %, about 30.7 wt %, about 30.8 wt %, about 30.9 wt %, about 31.0 wt %, about 31.1 wt %, about 31.2 wt %, about 31.3 wt %, about 31.4 wt %, about 31.5 wt %, about 31.6 wt %, about 31.7 wt %, about 31.8 wt %, about 31.9 wt %, about 32.0 wt %, about 32.1 wt %, about 32.2 wt %, about 32.3 wt %, about 32.4 wt %, about 32.5 wt %, about 32.6 wt %, about 32.7 wt %, about 32.8 wt %, about 32.9 wt %, about 33.0 wt %, about 33.1 wt %, about 33.2 wt %, about 33.3 wt %, about 33.4 wt %, about 33.5 wt %, about 33.6 wt %, about 33.7 wt %, about 33.8 wt %, about 33.9 wt %, about 34.0 wt %, about 34.1 wt %, about 34.2 wt %, about 34.3 wt %, about 34.4 wt %, about 34.5 wt %, about 34.6 wt %, about 34.7 wt %, about 34.8 wt %, about 34.9 wt %, about 35.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract; wherein formulation comprises a therapeutically effective amount of azelaic acid, minoxidil, finasteride, and duasteride; and the formulation comprises a silicone base in an amount of about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %, about 20.1 wt %, about 20.2 wt %, about 20.3 wt %, about 20.4 wt %, about 20.5 wt %, about 20.6 wt %, about 20.7 wt %, about 20.8 wt %, about 20.9 wt %, about 21.0 wt %, about 21.1 wt %, about 21.2 wt %, about 21.3 wt %, about 21.4 wt %, about 21.5 wt %, about 21.6 wt %, about 21.7 wt %, about 21.8 wt %, about 21.9 wt %, about 22.0 wt %, about 22.1 wt %, about 22.2 wt %, about 22.3 wt %, about 22.4 wt %, about 22.5 wt %, about 22.6 wt %, about 22.7 wt %, about 22.8 wt %, about 22.9 wt %, about 23.0 wt %, about 23.1 wt %, about 23.2 wt %, about 23.3 wt %, about 23.4 wt %, about 23.5 wt %, about 23.6 wt %, about 23.7 wt %, about 23.8 wt %, about 23.9 wt %, about 24.0 wt %, about 24.1 wt %, about 24.2 wt %, about 24.3 wt %, about 24.4 wt %, about 24.5 wt %, about 24.6 wt %, about 24.7 wt %, about 24.8 wt %, about 24.9 wt %, about 25.0 wt %, about 25.1 wt %, about 25.2 wt %, about 25.3 wt %, about 25.4 wt %, about 25.5 wt %, about 25.6 wt %, about 25.7 wt %, about 25.8 wt %, about 25.9 wt %, about 26.0 wt %, about 26.1 wt %, about 26.2 wt %, about 26.3 wt %, about 26.4 wt %, about 26.5 wt %, about 26.6 wt %, about 26.7 wt %, about 26.8 wt %, about 26.9 wt %, about 27.0 wt %, about 27.1 wt %, about 27.2 wt %, about 27.3 wt %, about 27.4 wt %, about 27.5 wt %, about 27.6 wt %, about 27.7 wt %, about 27.8 wt %, about 27.9 wt %, about 28.0 wt %, about 28.1 wt %, about 28.2 wt %, about 28.3 wt %, about 28.4 wt %, about 28.5 wt %, about 28.6 wt %, about 28.7 wt %, about 28.8 wt %, about 28.9 wt %, about 29.0 wt %, about 29.1 wt %, about 29.2 wt %, about 29.3 wt %, about 29.4 wt %, about 29.5 wt %, about 29.6 wt %, about 29.7 wt %, about 29.8 wt %, about 29.9 wt %, about 30.0 wt %, about 30.1 wt %, about 30.2 wt %, about 30.3 wt %, about 30.4 wt %, about 30.5 wt %, about 30.6 wt %, about 30.7 wt %, about 30.8 wt %, about 30.9 wt %, about 31.0 wt %, about 31.1 wt %, about 31.2 wt %, about 31.3 wt %, about 31.4 wt %, about 31.5 wt %, about 31.6 wt %, about 31.7 wt %, about 31.8 wt %, about 31.9 wt %, about 32.0 wt %, about 32.1 wt %, about 32.2 wt %, about 32.3 wt %, about 32.4 wt %, about 32.5 wt %, about 32.6 wt %, about 32.7 wt %, about 32.8 wt %, about 32.9 wt %, about 33.0 wt %, about 33.1 wt %, about 33.2 wt %, about 33.3 wt %, about 33.4 wt %, about 33.5 wt %, about 33.6 wt %, about 33.7 wt %, about 33.8 wt %, about 33.9 wt %, about 34.0 wt %, about 34.1 wt %, about 34.2 wt %, about 34.3 wt %, about 34.4 wt %, about 34.5 wt %, about 34.6 wt %, about 34.7 wt %, about 34.8 wt %, about 34.9 wt %, about 35.0 wt %, about 35.1 wt %, about 35.2 wt %, about 35.3 wt %, about 35.4 wt %, about 35.5 wt %, about 35.6 wt %, about 35.7 wt %, about 35.8 wt %, about 35.9 wt %, about 36.0 wt %, about 36.1 wt %, about 36.2 wt %, about 36.3 wt %, about 36.4 wt %, about 36.5 wt %, about 36.6 wt %, about 36.7 wt %, about 36.8 wt %, about 36.9 wt %, about 37.0 wt %, about 37.1 wt %, about 37.2 wt %, about 37.3 wt %, about 37.4 wt %, about 37.5 wt %, about 37.6 wt %, about 37.7 wt %, about 37.8 wt %, about 37.9 wt %, about 38.0 wt %, about 38.1 wt %, about 38.2 wt %, about 38.3 wt %, about 38.4 wt %, about 38.5 wt %, about 38.6 wt %, about 38.7 wt %, about 38.8 wt %, about 38.9 wt %, about 39.0 wt %, about 39.1 wt %, about 39.2 wt %, about 39.3 wt %, about 39.4 wt %, about 39.5 wt %, about 39.6 wt %, about 39.7 wt %, about 39.8 wt %, about 39.9 wt %, about 40.0 wt %, about 40.1 wt %, about 40.2 wt %, about 40.3 wt %, about 40.4 wt %, about 40.5 wt %, about 40.6 wt %, about 40.7 wt %, about 40.8 wt %, about 40.9 wt %, about 41.0 wt %, about 41.1 wt %, about 41.2 wt %, about 41.3 wt %, about 41.4 wt %, about 41.5 wt %, about 41.6 wt %, about 41.7 wt %, about 41.8 wt %, about 41.9 wt %, about 42.0 wt %, about 42.1 wt %, about 42.2 wt %, about 42.3 wt %, about 42.4 wt %, about 42.5 wt %, about 42.6 wt %, about 42.7 wt %, about 42.8 wt %, about 42.9 wt %, about 43.0 wt %, about 43.1 wt %, about 43.2 wt %, about 43.3 wt %, about 43.4 wt %, about 43.5 wt %, about 43.6 wt %, about 43.7 wt %, about 43.8 wt %, about 43.9 wt %, about 44.0 wt %, about 44.1 wt %, about 44.2 wt %, about 44.3 wt %, about 44.4 wt %, about 44.5 wt %, about 44.6 wt %, about 44.7 wt %, about 44.8 wt %, about 44.9 wt %, about 45.0 wt %, about 45.1 wt %, about 45.2 wt %, about 45.3 wt %, about 45.4 wt %, about 45.5 wt %, about 45.6 wt %, about 45.7 wt %, about 45.8 wt %, about 45.9 wt %, about 46.0 wt %, about 46.1 wt %, about 46.2 wt %, about 46.3 wt %, about 46.4 wt %, about 46.5 wt %, about 46.6 wt %, about 46.7 wt %, about 46.8 wt %, about 46.9 wt %, about 47.0 wt %, about 47.1 wt %, about 47.2 wt %, about 47.3 wt %, about 47.4 wt %, about 47.5 wt %, about 47.6 wt %, about 47.7 wt %, about 47.8 wt %, about 47.9 wt %, about 48.0 wt %, about 48.1 wt %, about 48.2 wt %, about 48.3 wt %, about 48.4 wt %, about 48.5 wt %, about 48.6 wt %, about 48.7 wt %, about 48.8 wt %, about 48.9 wt %, about 49.0 wt %, about 49.1 wt %, about 49.2 wt %, about 49.3 wt %, about 49.4 wt %, about 49.5 wt %, about 49.6 wt %, about 49.7 wt %, about 49.8 wt %, about 49.9 wt %, about 50.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract; wherein formulation comprises a therapeutically effective amount of azelaic acid, minoxidil, finasteride, and duasteride; wherein the formulation comprises one or more compounding agent in a disclosed amount; and wherein the formulation comprises caffeine present in an amount of about 0.00010 wt %, about 0.00015 wt %, about 0.00020 wt %, about 0.0025 wt %, about 0.00030 wt %, about 0.00035 wt %, about 0.00040 wt %, about 0.00045 wt %, about 0.00050 wt %, about 0.00055 wt %, about 0.00060 wt %, about 0.00065 wt %, about 0.00070 wt %, about 0.00075 wt %, about 0.00080 wt %, about 0.00085 wt %, about 0.00090 wt %, about 0.00095 wt %, about 0.00100 wt %, about 0.00105 wt %, about 0.00110 wt %, about 0.00115 wt %, about 0.00120 wt %, about 0.00125 wt %, about 0.00130 wt %, about 0.00135 wt %, about 0.00140 wt %, about 0.00145 wt %, about 0.00150 wt %, about 0.00155 wt %, about 0.00160 wt %, about 0.00165 wt %, about 0.00170 wt %, about 0.00175 wt %, about 0.00180 wt %, about 0.00185 wt %, about 0.00190 wt %, about 0.00195 wt %, about 0.0020 wt %, about 0.0025 wt %, about 0.0030 wt %, about 0.0035 wt %, about 0.0040 wt %, about 0.0045 wt %, about 0.0050 wt %, about 0.0055 wt %, about 0.0060 wt %, about 0.0065 wt %, about 0.0070 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract; wherein formulation comprises a therapeutically effective amount of azelaic acid, minoxidil, finasteride, and duasteride; wherein the formulation comprises one or more compounding agent in a disclosed amount; and wherein the formulation comprises saw palmetto extract present in an amount of about 0.10 wt %, about 0.20 wt %, about 0.30 wt %, about 0.40 wt %, about 0.50 wt %, about 0.60 wt %, about 0.70 wt %, about 0.80 wt %, about 0.90 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %, about 10.1 wt %, about 10.2 wt %, about 10.3 wt %, about 10.4 wt %, about 10.5 wt %, about 10.6 wt %, about 10.7 wt %, about 10.8 wt %, about 10.9 wt %, about 11.0 wt %, about 11.1 wt %, about 11.2 wt %, about 11.3 wt %, about 11.4 wt %, about 11.5 wt %, about 11.6 wt %, about 11.7 wt %, about 11.8 wt %, about 11.9 wt %, about 12.0 wt %, about 12.1 wt %, about 12.2 wt %, about 12.3 wt %, about 12.4 wt %, about 12.5 wt %, about 12.6 wt %, about 12.7 wt %, about 12.8 wt %, about 12.9 wt %, about 13.0 wt %, about 13.1 wt %, about 13.2 wt %, about 13.3 wt %, about 13.4 wt %, about 13.5 wt %, about 13.6 wt %, about 13.7 wt %, about 13.8 wt %, about 13.9 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising: a therapeutic composition comprising therapeutically effective amounts of azelaic acid, minoxidil, finasteride, and duasteride; one or more compounding agents; and optionally caffeine and/or saw palmetto extract; wherein formulation comprises a therapeutically effective amount of azelaic acid, minoxidil, finasteride, and duasteride; wherein the formulation comprises one or more compounding agent in a disclosed amount; wherein the formulation comprises caffeine present in an amount of about 0.00010 wt %, about 0.00015 wt %, about 0.00020 wt %, about 0.0025 wt %, about 0.00030 wt %, about 0.00035 wt %, about 0.00040 wt %, about 0.00045 wt %, about 0.00050 wt %, about 0.00055 wt %, about 0.00060 wt %, about 0.00065 wt %, about 0.00070 wt %, about 0.00075 wt %, about 0.00080 wt %, about 0.00085 wt %, about 0.00090 wt %, about 0.00095 wt %, about 0.00100 wt %, about 0.00105 wt %, about 0.00110 wt %, about 0.00115 wt %, about 0.00120 wt %, about 0.00125 wt %, about 0.00130 wt %, about 0.00135 wt %, about 0.00140 wt %, about 0.00145 wt %, about 0.00150 wt %, about 0.00155 wt %, about 0.00160 wt %, about 0.00165 wt %, about 0.00170 wt %, about 0.00175 wt %, about 0.00180 wt %, about 0.00185 wt %, about 0.00190 wt %, about 0.00195 wt %, about 0.0020 wt %, about 0.0025 wt %, about 0.0030 wt %, about 0.0035 wt %, about 0.0040 wt %, about 0.0045 wt %, about 0.0050 wt %, about 0.0055 wt %, about 0.0060 wt %, about 0.0065 wt %, about 0.0070 wt %; or any range encompassed by the foregoing values; or any combination of the foregoing values; and wherein the formulation comprises saw palmetto extract present in an amount of about 0.10 wt %, about 0.20 wt %, about 0.30 wt %, about 0.40 wt %, about 0.50 wt %, about 0.60 wt %, about 0.70 wt %, about 0.80 wt %, about 0.90 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %, about 10.1 wt %, about 10.2 wt %, about 10.3 wt %, about 10.4 wt %, about 10.5 wt %, about 10.6 wt %, about 10.7 wt %, about 10.8 wt %, about 10.9 wt %, about 11.0 wt %, about 11.1 wt %, about 11.2 wt %, about 11.3 wt %, about 11.4 wt %, about 11.5 wt %, about 11.6 wt %, about 11.7 wt %, about 11.8 wt %, about 11.9 wt %, about 12.0 wt %, about 12.1 wt %, about 12.2 wt %, about 12.3 wt %, about 12.4 wt %, about 12.5 wt %, about 12.6 wt %, about 12.7 wt %, about 12.8 wt %, about 12.9 wt %, about 13.0 wt %, about 13.1 wt %, about 13.2 wt %, about 13.3 wt %, about 13.4 wt %, about 13.5 wt %, about 13.6 wt %, about 13.7 wt %, about 13.8 wt %, about 13.9 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %; or any range encompassed by the foregoing values; or any combination of the foregoing values.

In a further aspect, the present disclosure pertains to topical formulations for treatment of hair loss and/or to increase hair growth, the formulation comprising: a therapeutic composition comprising therapeutically effective amounts of azelaic acid and minoxidil; one or more compounding agents; and optionally caffeine and/or saw palmetto extract.

In a further aspect, the disclosed topical formulation comprising therapeutically effective amounts of azelaic acid and minoxidil; one or more compounding agents; and optionally caffeine and/or saw palmetto extract; wherein the formulation comprises therapeutically effective amounts of azelaic acid and minoxidil as follows: about 0.100 wt % to about 0.500 wt % azelaic acid; and about 10 wt % to about 20 wt % minoxidil; wherein the wt % of a component is based on the total weight of the therapeutic composition; and one or more compound agents.

In a further aspect, the disclosed topical formulation comprising therapeutically effective amounts of azelaic acid and minoxidil; one or more compounding agents; and optionally caffeine and/or saw palmetto extract; wherein the formulation comprises therapeutically effective amounts of azelaic acid and minoxidil as follows: about 0.300 wt % to about 0.400 wt % azelaic acid; and about 12 wt % to about 17 wt % minoxidil; wherein the wt % of a component is based on the total weight of the therapeutic composition; and one or more compounding agents.

In a further aspect, the disclosed topical formulation comprising therapeutically effective amounts of azelaic acid and minoxidil; one or more compounding agents; and optionally caffeine and/or saw palmetto extract; wherein the formulation comprises therapeutically effective amounts of azelaic acid, minoxidil, finasteride, and duasteride as follows: about 0.325 wt % azelaic acid and about 15 wt % minoxidil; wherein the wt % of a component is based on the total weight of the therapeutic composition and one or more compounding agents.

In a further aspect, the disclosed topical formulation comprising therapeutically effective amounts of azelaic acid and minoxidil; one or more compounding agents; and optionally caffeine and/or saw palmetto extract; wherein the azelaic acid is present in an amount of about 0.100 wt %, about 0.105 wt %, about 0.110 wt %, about 0.115 wt %, about 0.120 wt %, about 0.125 wt %, about 0.130 wt %, about 0.135 wt %, about 0.140 wt %, about 0.145 wt %, about 0.150 wt %, about 0.155 wt %, about 0.160 wt %, about 0.165 wt %, about 0.170 wt %, about 0.175 wt %, about 0.180 wt %, about 0.185 wt %, about 0.190 wt %, about 0.195 wt %, about 0.200 wt %, about 0.205 wt %, about 0.210 wt %, about 0.215 wt %, about 0.220 wt %, about 0.225 wt %, about 0.230 wt %, about 0.235 wt %, about 0.240 wt %, about 0.245 wt %, about 0.250 wt %, about 0.255 wt %, about 0.260 wt %, about 0.265 wt %, about 0.270 wt %, about 0.275 wt %, about 0.280 wt %, about 0.285 wt %, about 0.290 wt %, about 0.295 wt %, about 0.300 wt %, about 0.305 wt %, about 0.310 wt %, about 0.315 wt %, about 0.320 wt %, about 0.325 wt %, about 0.330 wt %, about 0.335 wt %, about 0.340 wt %, about 0.345 wt %, about 0.350 wt %, about 0.355 wt %, about 0.360 wt %, about 0.365 wt %, about 0.370 wt %, about 0.375 wt %, about 0.380 wt %, about 0.385 wt %, about 0.390 wt %, about 0.395 wt %, about 0.400 wt %, about 0.405 wt %, about 0.410 wt %, about 0.415 wt %, about 0.420 wt %, about 0.425 wt %, about 0.430 wt %, about 0.435 wt %, about 0.440 wt %, about 0.445 wt %, about 0.450 wt %, about 0.455 wt %, about 0.460 wt %, about 0.465 wt %, about 0.470 wt %, about 0.475 wt %, about 0.480 wt %, about 0.485 wt %, about 0.490 wt %, about 0.495 wt %, about 0.500 wt %; or any range encompassed by the foregoing values; or any combination of the foregoing values.

In a further aspect, the disclosed topical formulation comprising therapeutically effective amounts of azelaic acid and minoxidil; one or more compounding agents; and optionally caffeine and/or saw palmetto extract; wherein the minoxidil is present in an amount of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %, about 10.1 wt %, about 10.2 wt %, about 10.3 wt %, about 10.4 wt %, about 10.5 wt %, about 10.6 wt %, about 10.7 wt %, about 10.8 wt %, about 10.9 wt %, about 11.0 wt %, about 11.1 wt %, about 11.2 wt %, about 11.3 wt %, about 11.4 wt %, about 11.5 wt %, about 11.6 wt %, about 11.7 wt %, about 11.8 wt %, about 11.9 wt %, about 12.0 wt %, about 12.1 wt %, about 12.2 wt %, about 12.3 wt %, about 12.4 wt %, about 12.5 wt %, about 12.6 wt %, about 12.7 wt %, about 12.8 wt %, about 12.9 wt %, about 13.0 wt %, about 13.1 wt %, about 13.2 wt %, about 13.3 wt %, about 13.4 wt %, about 13.5 wt %, about 13.6 wt %, about 13.7 wt %, about 13.8 wt %, about 13.9 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %; or any range encompassed by the foregoing values; or any combination of the foregoing values.

In various aspects, the present disclosure pertains to topical formulations for treatment of hair loss and/or to increase hair growth, the formulation comprising: a therapeutic composition comprising azelaic acid and minoxidil; one or more compounding agents; and optionally caffeine and/or saw palmetto extract; wherein the one or more compounding agents comprise ethoxy diglycol, propylene glycol, a gel base for gel-cream emulsions, a cream base, a silicone base, or combinations thereof.

In various aspects, the present disclosure pertains to topical formulations for treatment of hair loss and/or to increase hair growth, the formulation comprising: a therapeutic composition comprising azelaic acid and minoxidil; one or more compounding agents; and optionally caffeine and/or saw palmetto extract; wherein formulation comprises a therapeutically effective amount of azelaic acid and minoxidil; and the one or more compounding agents are present as follows: about 1 vol/wt % to about 10 vol/wt % ethoxy diglycol; about 1 vol/wt % to about 10 vol/wt % propylene glycol; about 5 wt % to about 20 wt % of a gel base for gel-cream emulsions; about 15 wt % to about 35 wt % of a cream base; and about 15 wt % to about 50 wt % of a silicone base; wherein the wt % of a component is based on the total weight of the therapeutic composition and one or more compounding agents; and wherein the vol/wt % of a component is based on the total weight of the therapeutic composition and one or more compounding agents.

In various aspects, the present disclosure pertains to topical formulations for treatment of hair loss and/or to increase hair growth, the formulation comprising: a therapeutic composition comprising azelaic acid and minoxidil; one or more compounding agents; and optionally caffeine and/or saw palmetto extract; wherein formulation comprises a therapeutically effective amount of azelaic acid and minoxidil; and the one or more compounding agents are present as follows: about 4 vol/wt % to about 6 vol/wt % ethoxy diglycol; about 2.5 vol/wt % to about 4.5 vol/wt % propylene glycol; about 8 wt % to about 14 wt % of a gel base for gel-cream emulsions; about 20 wt % to about 30 wt % of a cream base; and about 20 wt % to about 30 wt % of a silicone base; wherein the wt % of a component is based on the total weight of the therapeutic composition and one or more compounding agents; and wherein the vol/wt % of a component is based on the total weight of the therapeutic composition and one or more compounding agents.

In various aspects, the present disclosure pertains to topical formulations for treatment of hair loss and/or to increase hair growth, the formulation comprising: a therapeutic composition comprising azelaic acid and minoxidil; one or more compounding agents; and optionally caffeine and/or saw palmetto extract; wherein formulation comprises a therapeutically effective amount of azelaic acid and minoxidil; and the one or more compounding agents are present as follows: about 6 vol/wt % ethoxy diglycol; about 3.5 vol/wt % propylene glycol; about 11 wt % of a gel base for gel-cream emulsions; about 21 wt % to about 23 wt % of a cream base; and about 26 wt % to about 29 wt % of a silicone base; wherein the wt % of a component is based on the total weight of the therapeutic composition and one or more compounding agents; and wherein the vol/wt % of a component is based on the total weight of the therapeutic composition and one or more compounding agents.

In a further aspect, the present disclosure pertains to topical formulations for treatment of hair loss and/or to increase hair growth, the formulation comprising: a therapeutic composition comprising azelaic acid and minoxidil; one or more compounding agents; and optionally caffeine and/or saw palmetto extract; wherein formulation comprises a therapeutically effective amount of azelaic acid and minoxidil; and the formulation comprises ethoxy glycol in an amount of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %; or any range encompassed by the foregoing values; or any combination of the foregoing values.

In a further aspect, the present disclosure pertains to topical formulations for treatment of hair loss and/or to increase hair growth, the formulation comprising: a therapeutic composition comprising azelaic acid and minoxidil; one or more compounding agents; and optionally caffeine and/or saw palmetto extract; wherein formulation comprises a therapeutically effective amount of azelaic acid and minoxidil; and the formulation comprises propylene glycol in an amount of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %; or any range encompassed by the foregoing values; or any combination of the foregoing values.

In a further aspect, the present disclosure pertains to topical formulations for treatment of hair loss and/or to increase hair growth, the formulation comprising: a therapeutic composition comprising azelaic acid and minoxidil; one or more compounding agents; and optionally caffeine and/or saw palmetto extract; wherein formulation comprises a therapeutically effective amount of azelaic acid and minoxidil; and the formulation comprises a gel base for gel-cream emulsions in an amount of about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %, about 10.1 wt %, about 10.2 wt %, about 10.3 wt %, about 10.4 wt %, about 10.5 wt %, about 10.6 wt %, about 10.7 wt %, about 10.8 wt %, about 10.9 wt %, about 11.0 wt %, about 11.1 wt %, about 11.2 wt %, about 11.3 wt %, about 11.4 wt %, about 11.5 wt %, about 11.6 wt %, about 11.7 wt %, about 11.8 wt %, about 11.9 wt %, about 12.0 wt %, about 12.1 wt %, about 12.2 wt %, about 12.3 wt %, about 12.4 wt %, about 12.5 wt %, about 12.6 wt %, about 12.7 wt %, about 12.8 wt %, about 12.9 wt %, about 13.0 wt %, about 13.1 wt %, about 13.2 wt %, about 13.3 wt %, about 13.4 wt %, about 13.5 wt %, about 13.6 wt %, about 13.7 wt %, about 13.8 wt %, about 13.9 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %; or any range encompassed by the foregoing values; or any combination of the foregoing values.

In a further aspect, the present disclosure pertains to topical formulations for treatment of hair loss and/or to increase hair growth, the formulation comprising: a therapeutic composition comprising azelaic acid and minoxidil; one or more compounding agents; and optionally caffeine and/or saw palmetto extract; wherein formulation comprises a therapeutically effective amount of azelaic acid and minoxidil; and the formulation comprises a cream base in an amount of about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %, about 20.1 wt %, about 20.2 wt %, about 20.3 wt %, about 20.4 wt %, about 20.5 wt %, about 20.6 wt %, about 20.7 wt %, about 20.8 wt %, about 20.9 wt %, about 21.0 wt %, about 21.1 wt %, about 21.2 wt %, about 21.3 wt %, about 21.4 wt %, about 21.5 wt %, about 21.6 wt %, about 21.7 wt %, about 21.8 wt %, about 21.9 wt %, about 22.0 wt %, about 22.1 wt %, about 22.2 wt %, about 22.3 wt %, about 22.4 wt %, about 22.5 wt %, about 22.6 wt %, about 22.7 wt %, about 22.8 wt %, about 22.9 wt %, about 23.0 wt %, about 23.1 wt %, about 23.2 wt %, about 23.3 wt %, about 23.4 wt %, about 23.5 wt %, about 23.6 wt %, about 23.7 wt %, about 23.8 wt %, about 23.9 wt %, about 24.0 wt %, about 24.1 wt %, about 24.2 wt %, about 24.3 wt %, about 24.4 wt %, about 24.5 wt %, about 24.6 wt %, about 24.7 wt %, about 24.8 wt %, about 24.9 wt %, about 25.0 wt %, about 25.1 wt %, about 25.2 wt %, about 25.3 wt %, about 25.4 wt %, about 25.5 wt %, about 25.6 wt %, about 25.7 wt %, about 25.8 wt %, about 25.9 wt %, about 26.0 wt %, about 26.1 wt %, about 26.2 wt %, about 26.3 wt %, about 26.4 wt %, about 26.5 wt %, about 26.6 wt %, about 26.7 wt %, about 26.8 wt %, about 26.9 wt %, about 27.0 wt %, about 27.1 wt %, about 27.2 wt %, about 27.3 wt %, about 27.4 wt %, about 27.5 wt %, about 27.6 wt %, about 27.7 wt %, about 27.8 wt %, about 27.9 wt %, about 28.0 wt %, about 28.1 wt %, about 28.2 wt %, about 28.3 wt %, about 28.4 wt %, about 28.5 wt %, about 28.6 wt %, about 28.7 wt %, about 28.8 wt %, about 28.9 wt %, about 29.0 wt %, about 29.1 wt %, about 29.2 wt %, about 29.3 wt %, about 29.4 wt %, about 29.5 wt %, about 29.6 wt %, about 29.7 wt %, about 29.8 wt %, about 29.9 wt %, about 30.0 wt %, about 30.1 wt %, about 30.2 wt %, about 30.3 wt %, about 30.4 wt %, about 30.5 wt %, about 30.6 wt %, about 30.7 wt %, about 30.8 wt %, about 30.9 wt %, about 31.0 wt %, about 31.1 wt %, about 31.2 wt %, about 31.3 wt %, about 31.4 wt %, about 31.5 wt %, about 31.6 wt %, about 31.7 wt %, about 31.8 wt %, about 31.9 wt %, about 32.0 wt %, about 32.1 wt %, about 32.2 wt %, about 32.3 wt %, about 32.4 wt %, about 32.5 wt %, about 32.6 wt %, about 32.7 wt %, about 32.8 wt %, about 32.9 wt %, about 33.0 wt %, about 33.1 wt %, about 33.2 wt %, about 33.3 wt %, about 33.4 wt %, about 33.5 wt %, about 33.6 wt %, about 33.7 wt %, about 33.8 wt %, about 33.9 wt %, about 34.0 wt %, about 34.1 wt %, about 34.2 wt %, about 34.3 wt %, about 34.4 wt %, about 34.5 wt %, about 34.6 wt %, about 34.7 wt %, about 34.8 wt %, about 34.9 wt %, about 35.0 wt %; or any range encompassed by the foregoing values; or any combination of the foregoing values.

In a further aspect, the present disclosure pertains to topical formulations for treatment of hair loss and/or to increase hair growth, the formulation comprising: a therapeutic composition comprising azelaic acid and minoxidil; one or more compounding agents; and optionally caffeine and/or saw palmetto extract; wherein formulation comprises a therapeutically effective amount of azelaic acid and minoxidil; and the formulation comprises a silicone base in an amount of about 15.0 wt %, about 15.1 wt %, about 15.2 wt %, about 15.3 wt %, about 15.4 wt %, about 15.5 wt %, about 15.6 wt %, about 15.7 wt %, about 15.8 wt %, about 15.9 wt %, about 16.0 wt %, about 16.1 wt %, about 16.2 wt %, about 16.3 wt %, about 16.4 wt %, about 16.5 wt %, about 16.6 wt %, about 16.7 wt %, about 16.8 wt %, about 16.9 wt %, about 17.0 wt %, about 17.1 wt %, about 17.2 wt %, about 17.3 wt %, about 17.4 wt %, about 17.5 wt %, about 17.6 wt %, about 17.7 wt %, about 17.8 wt %, about 17.9 wt %, about 18.0 wt %, about 18.1 wt %, about 18.2 wt %, about 18.3 wt %, about 18.4 wt %, about 18.5 wt %, about 18.6 wt %, about 18.7 wt %, about 18.8 wt %, about 18.9 wt %, about 19.0 wt %, about 19.1 wt %, about 19.2 wt %, about 19.3 wt %, about 19.4 wt %, about 19.5 wt %, about 19.6 wt %, about 19.7 wt %, about 19.8 wt %, about 19.9 wt %, about 20.0 wt %, about 20.1 wt %, about 20.2 wt %, about 20.3 wt %, about 20.4 wt %, about 20.5 wt %, about 20.6 wt %, about 20.7 wt %, about 20.8 wt %, about 20.9 wt %, about 21.0 wt %, about 21.1 wt %, about 21.2 wt %, about 21.3 wt %, about 21.4 wt %, about 21.5 wt %, about 21.6 wt %, about 21.7 wt %, about 21.8 wt %, about 21.9 wt %, about 22.0 wt %, about 22.1 wt %, about 22.2 wt %, about 22.3 wt %, about 22.4 wt %, about 22.5 wt %, about 22.6 wt %, about 22.7 wt %, about 22.8 wt %, about 22.9 wt %, about 23.0 wt %, about 23.1 wt %, about 23.2 wt %, about 23.3 wt %, about 23.4 wt %, about 23.5 wt %, about 23.6 wt %, about 23.7 wt %, about 23.8 wt %, about 23.9 wt %, about 24.0 wt %, about 24.1 wt %, about 24.2 wt %, about 24.3 wt %, about 24.4 wt %, about 24.5 wt %, about 24.6 wt %, about 24.7 wt %, about 24.8 wt %, about 24.9 wt %, about 25.0 wt %, about 25.1 wt %, about 25.2 wt %, about 25.3 wt %, about 25.4 wt %, about 25.5 wt %, about 25.6 wt %, about 25.7 wt %, about 25.8 wt %, about 25.9 wt %, about 26.0 wt %, about 26.1 wt %, about 26.2 wt %, about 26.3 wt %, about 26.4 wt %, about 26.5 wt %, about 26.6 wt %, about 26.7 wt %, about 26.8 wt %, about 26.9 wt %, about 27.0 wt %, about 27.1 wt %, about 27.2 wt %, about 27.3 wt %, about 27.4 wt %, about 27.5 wt %, about 27.6 wt %, about 27.7 wt %, about 27.8 wt %, about 27.9 wt %, about 28.0 wt %, about 28.1 wt %, about 28.2 wt %, about 28.3 wt %, about 28.4 wt %, about 28.5 wt %, about 28.6 wt %, about 28.7 wt %, about 28.8 wt %, about 28.9 wt %, about 29.0 wt %, about 29.1 wt %, about 29.2 wt %, about 29.3 wt %, about 29.4 wt %, about 29.5 wt %, about 29.6 wt %, about 29.7 wt %, about 29.8 wt %, about 29.9 wt %, about 30.0 wt %, about 30.1 wt %, about 30.2 wt %, about 30.3 wt %, about 30.4 wt %, about 30.5 wt %, about 30.6 wt %, about 30.7 wt %, about 30.8 wt %, about 30.9 wt %, about 31.0 wt %, about 31.1 wt %, about 31.2 wt %, about 31.3 wt %, about 31.4 wt %, about 31.5 wt %, about 31.6 wt %, about 31.7 wt %, about 31.8 wt %, about 31.9 wt %, about 32.0 wt %, about 32.1 wt %, about 32.2 wt %, about 32.3 wt %, about 32.4 wt %, about 32.5 wt %, about 32.6 wt %, about 32.7 wt %, about 32.8 wt %, about 32.9 wt %, about 33.0 wt %, about 33.1 wt %, about 33.2 wt %, about 33.3 wt %, about 33.4 wt %, about 33.5 wt %, about 33.6 wt %, about 33.7 wt %, about 33.8 wt %, about 33.9 wt %, about 34.0 wt %, about 34.1 wt %, about 34.2 wt %, about 34.3 wt %, about 34.4 wt %, about 34.5 wt %, about 34.6 wt %, about 34.7 wt %, about 34.8 wt %, about 34.9 wt %, about 35.0 wt %, about 35.1 wt %, about 35.2 wt %, about 35.3 wt %, about 35.4 wt %, about 35.5 wt %, about 35.6 wt %, about 35.7 wt %, about 35.8 wt %, about 35.9 wt %, about 36.0 wt %, about 36.1 wt %, about 36.2 wt %, about 36.3 wt %, about 36.4 wt %, about 36.5 wt %, about 36.6 wt %, about 36.7 wt %, about 36.8 wt %, about 36.9 wt %, about 37.0 wt %, about 37.1 wt %, about 37.2 wt %, about 37.3 wt %, about 37.4 wt %, about 37.5 wt %, about 37.6 wt %, about 37.7 wt %, about 37.8 wt %, about 37.9 wt %, about 38.0 wt %, about 38.1 wt %, about 38.2 wt %, about 38.3 wt %, about 38.4 wt %, about 38.5 wt %, about 38.6 wt %, about 38.7 wt %, about 38.8 wt %, about 38.9 wt %, about 39.0 wt %, about 39.1 wt %, about 39.2 wt %, about 39.3 wt %, about 39.4 wt %, about 39.5 wt %, about 39.6 wt %, about 39.7 wt %, about 39.8 wt %, about 39.9 wt %, about 40.0 wt %, about 40.1 wt %, about 40.2 wt %, about 40.3 wt %, about 40.4 wt %, about 40.5 wt %, about 40.6 wt %, about 40.7 wt %, about 40.8 wt %, about 40.9 wt %, about 41.0 wt %, about 41.1 wt %, about 41.2 wt %, about 41.3 wt %, about 41.4 wt %, about 41.5 wt %, about 41.6 wt %, about 41.7 wt %, about 41.8 wt %, about 41.9 wt %, about 42.0 wt %, about 42.1 wt %, about 42.2 wt %, about 42.3 wt %, about 42.4 wt %, about 42.5 wt %, about 42.6 wt %, about 42.7 wt %, about 42.8 wt %, about 42.9 wt %, about 43.0 wt %, about 43.1 wt %, about 43.2 wt %, about 43.3 wt %, about 43.4 wt %, about 43.5 wt %, about 43.6 wt %, about 43.7 wt %, about 43.8 wt %, about 43.9 wt %, about 44.0 wt %, about 44.1 wt %, about 44.2 wt %, about 44.3 wt %, about 44.4 wt %, about 44.5 wt %, about 44.6 wt %, about 44.7 wt %, about 44.8 wt %, about 44.9 wt %, about 45.0 wt %, about 45.1 wt %, about 45.2 wt %, about 45.3 wt %, about 45.4 wt %, about 45.5 wt %, about 45.6 wt %, about 45.7 wt %, about 45.8 wt %, about 45.9 wt %, about 46.0 wt %, about 46.1 wt %, about 46.2 wt %, about 46.3 wt %, about 46.4 wt %, about 46.5 wt %, about 46.6 wt %, about 46.7 wt %, about 46.8 wt %, about 46.9 wt %, about 47.0 wt %, about 47.1 wt %, about 47.2 wt %, about 47.3 wt %, about 47.4 wt %, about 47.5 wt %, about 47.6 wt %, about 47.7 wt %, about 47.8 wt %, about 47.9 wt %, about 48.0 wt %, about 48.1 wt %, about 48.2 wt %, about 48.3 wt %, about 48.4 wt %, about 48.5 wt %, about 48.6 wt %, about 48.7 wt %, about 48.8 wt %, about 48.9 wt %, about 49.0 wt %, about 49.1 wt %, about 49.2 wt %, about 49.3 wt %, about 49.4 wt %, about 49.5 wt %, about 49.6 wt %, about 49.7 wt %, about 49.8 wt %, about 49.9 wt %, about 50.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising: a therapeutic composition comprising azelaic acid, minoxidil, finasteride, and duasteride; one or more compounding agents; and optionally caffeine and/or saw palmetto extract; wherein formulation comprises a therapeutically effective amount of azelaic acid and minoxidil; wherein the formulation comprises one or more compounding agent in a disclosed amount; and wherein the formulation comprises caffeine present in an amount of about 0.00010 wt %, about 0.00015 wt %, about 0.00020 wt %, about 0.0025 wt %, about 0.00030 wt %, about 0.00035 wt %, about 0.00040 wt %, about 0.00045 wt %, about 0.00050 wt %, about 0.00055 wt %, about 0.00060 wt %, about 0.00065 wt %, about 0.00070 wt %, about 0.00075 wt %, about 0.00080 wt %, about 0.00085 wt %, about 0.00090 wt %, about 0.00095 wt %, about 0.00100 wt %, about 0.00105 wt %, about 0.00110 wt %, about 0.00115 wt %, about 0.00120 wt %, about 0.00125 wt %, about 0.00130 wt %, about 0.00135 wt %, about 0.00140 wt %, about 0.00145 wt %, about 0.00150 wt %, about 0.00155 wt %, about 0.00160 wt %, about 0.00165 wt %, about 0.00170 wt %, about 0.00175 wt %, about 0.00180 wt %, about 0.00185 wt %, about 0.00190 wt %, about 0.00195 wt %, about 0.0020 wt %, about 0.0025 wt %, about 0.0030 wt %, about 0.0035 wt %, about 0.0040 wt %, about 0.0045 wt %, about 0.0050 wt %, about 0.0055 wt %, about 0.0060 wt %, about 0.0065 wt %, about 0.0070 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising azelaic acid and minoxidil; one or more compounding agents; and optionally caffeine and/or saw palmetto extract; wherein formulation comprises a therapeutically effective amount of azelaic acid and minoxidil; wherein the formulation comprises one or more compounding agent in a disclosed amount; and wherein the formulation comprises saw palmetto extract present in an amount of about 0.10 wt %, about 0.20 wt %, about 0.30 wt %, about 0.40 wt %, about 0.50 wt %, about 0.60 wt %, about 0.70 wt %, about 0.80 wt %, about 0.90 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %, about 10.1 wt %, about 10.2 wt %, about 10.3 wt %, about 10.4 wt %, about 10.5 wt %, about 10.6 wt %, about 10.7 wt %, about 10.8 wt %, about 10.9 wt %, about 11.0 wt %, about 11.1 wt %, about 11.2 wt %, about 11.3 wt %, about 11.4 wt %, about 11.5 wt %, about 11.6 wt %, about 11.7 wt %, about 11.8 wt %, about 11.9 wt %, about 12.0 wt %, about 12.1 wt %, about 12.2 wt %, about 12.3 wt %, about 12.4 wt %, about 12.5 wt %, about 12.6 wt %, about 12.7 wt %, about 12.8 wt %, about 12.9 wt %, about 13.0 wt %, about 13.1 wt %, about 13.2 wt %, about 13.3 wt %, about 13.4 wt %, about 13.5 wt %, about 13.6 wt %, about 13.7 wt %, about 13.8 wt %, about 13.9 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %; or any range encompassed by the foregoing values; or any combination of the foregoing values.

In a further aspect, the disclosed topical formulation the present disclosure pertains to topical formulations for treatment of hair loss and/or to increase hair growth, the formulation comprising: a therapeutic composition comprising azelaic acid and minoxidil; one or more compounding agents; and optionally caffeine and/or saw palmetto extract; wherein formulation comprises a therapeutically effective amount of azelaic acid and minoxidil; wherein the formulation comprises one or more compounding agent in a disclosed amount; wherein the formulation comprises caffeine present in an amount of about 0.00010 wt %, about 0.00015 wt %, about 0.00020 wt %, about 0.0025 wt %, about 0.00030 wt %, about 0.00035 wt %, about 0.00040 wt %, about 0.00045 wt %, about 0.00050 wt %, about 0.00055 wt %, about 0.00060 wt %, about 0.00065 wt %, about 0.00070 wt %, about 0.00075 wt %, about 0.00080 wt %, about 0.00085 wt %, about 0.00090 wt %, about 0.00095 wt %, about 0.00100 wt %, about 0.00105 wt %, about 0.00110 wt %, about 0.00115 wt %, about 0.00120 wt %, about 0.00125 wt %, about 0.00130 wt %, about 0.00135 wt %, about 0.00140 wt %, about 0.00145 wt %, about 0.00150 wt %, about 0.00155 wt %, about 0.00160 wt %, about 0.00165 wt %, about 0.00170 wt %, about 0.00175 wt %, about 0.00180 wt %, about 0.00185 wt %, about 0.00190 wt %, about 0.00195 wt %, about 0.0020 wt %, about 0.0025 wt %, about 0.0030 wt %, about 0.0035 wt %, about 0.0040 wt %, about 0.0045 wt %, about 0.0050 wt %, about 0.0055 wt %, about 0.0060 wt %, about 0.0065 wt %, about 0.0070 wt %; or any range encompassed by the foregoing values; or any combination of the foregoing values; and wherein the formulation comprises saw palmetto extract present in an amount of about 0.10 wt %, about 0.20 wt %, about 0.30 wt %, about 0.40 wt %, about 0.50 wt %, about 0.60 wt %, about 0.70 wt %, about 0.80 wt %, about 0.90 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10.0 wt %, about 10.1 wt %, about 10.2 wt %, about 10.3 wt %, about 10.4 wt %, about 10.5 wt %, about 10.6 wt %, about 10.7 wt %, about 10.8 wt %, about 10.9 wt %, about 11.0 wt %, about 11.1 wt %, about 11.2 wt %, about 11.3 wt %, about 11.4 wt %, about 11.5 wt %, about 11.6 wt %, about 11.7 wt %, about 11.8 wt %, about 11.9 wt %, about 12.0 wt %, about 12.1 wt %, about 12.2 wt %, about 12.3 wt %, about 12.4 wt %, about 12.5 wt %, about 12.6 wt %, about 12.7 wt %, about 12.8 wt %, about 12.9 wt %, about 13.0 wt %, about 13.1 wt %, about 13.2 wt %, about 13.3 wt %, about 13.4 wt %, about 13.5 wt %, about 13.6 wt %, about 13.7 wt %, about 13.8 wt %, about 13.9 wt %, about 14.0 wt %, about 14.1 wt %, about 14.2 wt %, about 14.3 wt %, about 14.4 wt %, about 14.5 wt %, about 14.6 wt %, about 14.7 wt %, about 14.8 wt %, about 14.9 wt %, about 15.0 wt %; or any range encompassed by the foregoing values; or any combination of the foregoing values.

The topical formulations of the present disclosures may be formulated into a variety of topically administrable formulations, such as solutions, suspensions, lotions, gels, pastes, medicated sticks, balms, creams, ointments, foams or transdermal patches.

Topical formulations in the form of a topical solution tend to be of low viscosity, and often use water or alcohol as the base. They can be formed by dissolving powder in water, alcohol and sometimes oil. If alcohol is used as the base, it can cause drying of the skin. Lotions are similar to solutions but are thicker and tend to be more emollient in nature than solutions. Lotions usually have an oil mixed with water and, more often than not, have less alcohol than solutions.

A topical formulation in the form of a topical cream has an emulsion of oil and water in approximately equal proportions. It penetrates the stratum corneum outer layer of the skin well. Cream is thicker than lotion and maintains its shape when removed from its container. It tends to be moderate in moisturizing tendency.

A topical formulation in the form of a topical ointment is a homogeneous, semi-solid preparation, most commonly a greasy, thick oil (e.g., oil 80%-water 20%) with a high viscosity that is intended for external application to the skin or mucus membranes. Ointments are formulated using hydrophobic, hydrophilic or water-emulsifying bases to provide preparations that are immiscible, miscible or emulsifiable with skin secretions. Ointments can also be derived from hydrocarbon (fatty), absorption, water-removable or water-soluble bases. Gels are often a semisolid emulsion, such as cellulose, in an alcohol or acetone base.

A topical formulation in the form of a transdermal patch can be a very precise time release method of delivering a drug. The release of the active component from a transdermal patch may be controlled by diffusion through the adhesive which covers the whole patch, by diffusion through a membrane which may only have adhesive on the patch rim or controlled by release from a polymer matrix.

A suitable gel base for gel-cream emulsions is one that has one or more of the following characteristics: noncomedogenic, hypoallergenic, non-irritating, odor-free, comprises natural emulsifiers, non-ionic emulsion system that is compatible with cationic and anionic substances, and that is stable over a broad pH range, such as about pH 3.5 to pH12. An exemplary, but non-limiting example of a suitable gel base for gel-cream emulsions is the commercially available Versabase Gel® from Professional Compounding Pharmacies of America (PCCA; 9901 South Wilcrest Dr., Houston, Texas), and reportedly contains ammonium acryloyldimethyltaurate/VP Copolymer, aloe vera, edetate disodium, allantoin, methylchloroisothiazolinone and methylisothiazolinone. Versabase Gel® is designed as an inert base for compounding formulations for topical preparations. In a further aspect, a suitable gel base for gel-cream emulsions is chosen from the group consisting of VersaBase, LIPODERM, PENTRAVAN, Pluronic Lecithin Organogel (PLO), and mixtures thereof.

In some aspects, the gel base for gel-cream emulsions comprises water, ammonium acryloyldimethyltaurate copolymer, aloe barbadensis leaf juice powder, allatoin, disodium EDTA, methylchloroisothiazolinone and methylisothiazolinone. The ammonium acryloyldimethyltaurate/VP Copolymer may act as a gelling agent for the aqueous solution to allow for topical application without dripping or drying out. The aloe vera may enhance skin penetration of the active botanical constituents allowing for transdermal uptake. The allantoin may act as a keratolytic agent to improve moisture binding capacity of the epidermis to also improve drug penetration into the skin.

In further aspects, gel base for gel-cream emulsions with these activities, i.e., transdermal absorption and surface adhesion, may be used in a disclosed topical formulation. For example, other suitable gel base for gel-cream emulsions include: LIPODERM® (Professional Compounding Centers of America, Inc., Houston, Tex.), PENTRAVAN) (Fargon, Inc., St. Paul, Minn.), and Pluronic Lecithin Organogel. LIPODERM reportedly comprises ethoxydiglycol, water, glycerin, Cu-Cis alkyl benzoate, glyceryl stearate, dimethicone, cetearyl alcohol, cetearyl glucoside, polyacrylamide, cetyl alcohol, magnesium aluminum silicate, xanthan gum, aloe vera, tocopheryl acetate, bitter almond kernel oil, grape seed extract, wheat germ oil, vitamin-A palmitate, vitamin-C palmitate, ProLipo multi-emulsion liposomic system, tetrasodium EDTA, phenoxyethanol and sodium hydroxymethyl glycinate.

In a further aspect, rather than using commercially available bases such as these, ingredients similar to those found in these bases may be used to form new bases that can be used in the therapeutic compositions herein. For example, other fatty acids, fatty acid esters, alkoxylated fatty acids, alkoxylated fatty acid esters, monoglycerides, diglycerides, triglycerides, sorbitan fatty acid esters, fatty alcohols, oils, lipids, gums, polymers, and the like, may be compounded with the therapeutic agents discussed to produce therapeutic compositions within the scope of the present disclosure.

In various aspects, a disclosed topical formulation comprises a silicone base. For example, a suitable commercially available silicone base is a topical anhydrous silicone base such as PracaSil Plus™, manufactured by PCCA, and Scar Care Base Enhanced, manufactured by Letco Medical (1316 Commerce Drive NW, Decatur, Alabama 35601).

In a further aspect, a suitable silicone base can comprise dimethicone, dimethiconol, cyclopentasiloxane, cetyl dimethicone, phenyl trimethicone, low hexyl dimethicone, or combinations thereof. In a still further aspect, a suitable silicone base can comprise cyclopentasiloxane, polysilicone-11, C30-45 alkyl cetearyl dimethicone crosspolymer, dimethiconol, phenyl trimethicone, PEG PPG dimethicone, or combinations thereof. The silicone base can further comprise non-silicone components such as *Carapa guaianensis* seed oil, macadamia nut oil, laureth-4, PEG 30 dipolyhydroxystearate, or combinations thereof.

In a further aspect, a silicone base can comprise ingredients such as cyclopentasiloxane; polysilicone-11; dimethicone; and/or C30-45 alkyl cetearyl dimethicone crosspolymer. Briefly, cyclopentasiloxane is a type of silicone, and may have the ability to lubricate, and may be waterproof and provide shine. Cyclopentasiloxane may have a very sticky consistency, and may be volatile and/or used in combination with dimethicone. The cyclopentasiloxane may be combined with polysilicone-11, which may be a synthetic crosslinked siloxane that functions as a film-forming agent and polymer, and/or C30-45 alkyl cetearyl dimethicone crosspolymer, which may be a copolymer of C30-45 alkyl cetearyl dimethicone crosslinked with vinyl cyclohexene oxide, or another copolymer.

In another aspect, the silicone base may comprise silicone components, such as those disclosed by U.S. Pat. Nos. 6,827,929; 6,337,076; U.S. Publication No. 2011/0046532; U.S. Publication No. 2010/0322875; U.S. Publication No. 2009/0143333; and/or U.S. Publication No. 2006/0029672, which are all incorporated herein by reference in their entireties. Silicone bases having additional, fewer, or alternate ingredients may be used.

Without wishing to be bound by a particular theory, it is believed that the silicone base may facilitate the permeation of the therapeutic composition in the silicone base through the skin of a patient when the silicone base is topically applied. The silicone may be a polymer, such as plastic or rubber, containing silicon. Silicone variants or variations of silicone that may be used with the silicone base may include silicone or silicone derivatives that are in gel, fluid, powder, or other forms. The silicone or silicone variants may include silicon, silicon oxide, silicon dioxide, silica, medical grade silicone, professional grade silicone, or other forms of silicone and/or silicon.

In various aspects, the disclosed topical formulations can comprise a fatty acid. Any fatty acid, or combination of fatty acids, may be blended with the disclosed therapeutic agents herein to produce a disclosed topical formulation. For example, any $C_6$-$C_{24}$ fatty acid may be used in the pharmaceutical formulas of the present disclosure. Fatty acids for use herein also include $C_6$-$C_{24}$ fatty acids having any degree of unsaturation in the carbon chain. Fatty acids for use herein may be from natural oil and fat sources such as tallow, lard, coconut oil, palm oil, peanut oil, rice bran oil, olive oil, cottonseed oil, wheat germ oil, soy bean oil, corn oil, sunflower oil, and safflower oil, amongst others. Natural oils may supply a distribution of fatty acid chain lengths. For therapeutic compositions within the scope of the present disclosure, any combination of free fatty acid, natural oils, hydrogenated oils, partially hydrogenated oils, vegetable and animal fats, monoglycerides, diglycerides and triglycerides may be used, and may be combined with any other emulsifiers, emollients, carriers, solubilizers, solvents, and the like, as desired.

In certain aspects, the compositions comprise a thickening agent. The thickening agent may be monomeric, oligomeric or polymeric in its nature, or any combination of monomeric, oligomeric or polymeric thickening agents thereof.

Exemplary monomeric thickening agents include alcohols and esters, for example, fatty alcohols, esters of fatty alcohols, and fatty acid esters, any of which may be isolated from natural sources or synthetically derived. Fatty alcohols are exemplified by any $C_{12}$-$C_{24}$ straight chain or branched alcohol, or any combination of two or more $C_{12}$-$C_{24}$ straight chain or branched alcohols. By way of example, a fatty alcohol, preferably comprising cetyl alcohol or stearyl alcohol or combination thereof, may be present in the composition in the range of from about 0.05% to about 2% by weight, preferably from about 0.1% to about 1% by weight, more preferably from about 0.1% to about 0.5% by weight, with from about 0.1 to about 0.3% by weight being even more preferred. These fatty alcohols may be used alone or in conjunction with glyceryl esters of fatty acids or ethoxylated fatty acid esters, such as polyethylene glycol esters of fatty acids, or any combination thereof. Thickening agents may also be selected based on their hydrophilic-lipophilic balance. Typically, such thickening agents have emulsification or composition stiffening properties and will usually have and HLB value of from about 12 to about 16. These agents may assist in the formation of oil in water emulsions and provide certain desired viscosity properties to the final compositions. In some aspects, the thickening agent comprises glyceryl esters, preferably glyceryl esters of fatty acids, such as glyceryl stearate. Additional examples of alcohol ethoxylates may be found in *Kirk-Othmer Encyclopedia of Chemical Technology*, 3$^{rd}$, Edition, Volume 22, pages 364 and 365. Numerous examples of other glyceryl esters of fatty acids may be found in *Kirk-Othmer Encyclopedia of Chemical Technology*, 3$^{rd}$ Edition, Volume 22, pages 367 and 368. These esters may be used alone or in conjunction with ethoxylated fatty acid esters, such as polyethylene glycol esters of fatty acids. For example, in some aspects, a mixture of glyceryl stearate and PEG-100 stearate is employed as a thickening agent in the composition. Various combinations (ratios) of these two agents may be used by one of ordinary skill in the art to appropriately thicken or stiffen the composition to assist in its localization once applied to tissue. In certain preferred aspects, about 2 wt. parts of glyceryl stearate per wt. part of PEG-100 stearate provides satisfactory results when used at a combined weight level of from about 2% to about 12% by weight of the composition; preferably from about 3% to about 11% by weight; more preferably from about 4% to about 10% by weight; with from about 5% to about 10% by weight being even more preferred. Alternatively, polyethylene glycol esters of fatty acids may be used as thickening agents. In other alternative aspects, the thickening agent comprises silica. Additional organic or inorganic thickening agents are known in the art.

In still other aspects, the thickening agents comprise an anionic or non-ionic polymer or copolymer. In addition to their usefulness as thickeners, these anionic or non-ionic polymers or copolymers may also provide better substantivity. These features allow the compositions to be retained on the tissue even while being exposed to bodily fluids or sweat and the like, and yet, preferably, still be reasonably easily removed when desired with mild cleaning agents such as soap and water. Generally speaking, the anionic or non-ionic polymers or copolymers comprise hydrophilic and hydrophobic moieties. When more substantivity in the compositions of the present disclosure is desired, an anionic or non-ionic polymer or copolymer should be selected based on higher levels of hydrophobic moieties. When more fluidity is desired, the level of hydrophilic moieties should be increased relative to the hydrophobic moieties. Non-limiting examples generally include anionic or non-ionic acrylate copolymers or carbomers.

In some aspects preferred copolymer thickening agents comprise copolymers of ammonium acryloyldimethyltaurate and vinylpyrrolidone monomers, or copolymers of $C_{10}$-$C_{30}$ acrylate with monomers of acrylic acid or methacrylic acid or any combination thereof. Examples of some commercially available polymeric thickening agents include VersaBase Gel® (PCCA, 9901 South Wilcrest Drive Houston, Tex. 77099); Carbomer Gel (Letco Medical, 1316 Commerce Drive, NW Decatur, Ala. 35601); and Adaptaderm Gel (Freedom Pharmaceuticals, 801 W. New Orleans St., Broken Arrow, Okla. 74011).

In a further aspect, anionic acrylate copolymers include copolymers of acrylic acid, acrylamide, sodium acrylate and sodium acryloyldimethyltaurate monomers, such as, for example, Polyacrylate-13 and the like. While such polymers may be used as thickening agents alone, they may also be used in combination other known thickening agents including polyisobutene and/or polysorbitan polyethoxylates and their fatty acid esters, such as for example, Polysorbate 20. One such advantageous combination of Polyacrylate-13, Polyisobutene, and Polysorbate 20, known under the trade name SEPIPLUS™ 400, is provided by Société d'Exploitation de Produits Pour les Industries Chimiques, Paris France. In other alternative aspects, thickening agents comprise a non-ionic copolymer, such as for example, a poloxamer. Poloxamers are nonionic triblock copolymers composed of a central hydrophobic chain of polyoxypropylene (poly(propylene oxide)) flanked by two hydrophilic chains of polyoxyethylene (poly(ethylene oxide)) and have the general structure shown below wherein a=2-130 and b=15-67:

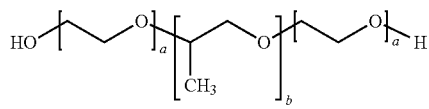

Because the lengths of the polymer blocks can be customized, many different poloxamers exist that have slightly different properties, which are well understood to those of ordinary skill in the art. Once armed with the disclosures herein, any of a number of poloxamers may be chosen for use dependent at least in part on the properties desired in the final product. Because of their amphiphilic structure, the polymers have surfactant properties that make them useful in industrial applications. Among other things, they can be used to increase the water solubility of hydrophobic, oily substances or otherwise increase the miscibility of two substances with different hydrophobicities. Typically, the poloxamers of the present disclosure have the structure of Formula I wherein each a is independently in the range of from about 80 to about 120, preferably from about 90 to about 110, and b is in the range of from about 50 to about 80, preferably from about 55 to about 70. In other alternative aspects, the typical the poloxamers have an approximate molecular mass of the poly(oxypropylene) core of 3500 to about 4500 g/mol and about 65 to about 75% of poly (oxyethylene) content by weight of the poloxamer. An exemplary poloxamer of this class for use in the compositions of the present disclosure is Poloxamer 407. Poloxamer 407 is a triblock copolymer which includes a central hydrophobic block of polypropylene glycol flanked by two hydrophilic blocks of polyethylene glycol. The approximate lengths of the two PEG blocks is 101 repeat units while the approximate length of the propylene glycol block is 56 repeat units. This particular compound is also known by the BASF trade name Pluronic F127 or by the Croda trade name Synperonic PE/F 127. In addition to viscosity modification properties, poloxamers, including Poloxamer 407, are known to incorporate into cellular membranes forming a biocompatible film. Without being held to theories of action, it is believed that formation of such a biocompatible film may allow the PVP/iodine element of the present disclosure to remain in contact with skin tissue such as that located on the scalp for extended periods of time Typically, anionic or non-ionic polymer or copolymer levels in antimicrobial compositions of the present disclosure are in the range of from about 0.1 to about 6% by weight of the composition, preferably from about 0.1 to about 5.5% by weight of the composition, still more preferably from about 2 to about 3% by weight of the composition. In combination-type polymer or co-polymer thickening agents, the relative ratio of the two or more components is not critical insofar as it does not interfere with the efficacy of the antimicrobial agent(s) and/or the substantivity on skin of the final composition. By way of guidance, a relative wt. ratio of Polyacrylate-13/Polyisobutene/Polysorbate 20 of from about 15:6:1 to about 10:5:1. In other aspects, the relative wt. ratio of Polyacrylate-13 to Polyisobutene in the formulation is from about 3:1 to about 1:3, and all combinations and subcombinations thereof. In certain other aspects, the relative wt. ratio of Polyacrylate-13 to Polysorbate 20 in the formulation is from about 5:1 to about 20:1, and all combinations and subcombinations thereof.

In yet other aspects, the thickening agents comprise a modified cellulose derivative such as, for example, non-ionic soluble cellulose ethers. Hydroxyethyl cellulose is an exemplary compound in this family, and is soluble in both hot and cold water. Hydroxyethyl cellulose has good water retention and film formation. Owing to good thickening, suspending, dispersing, emulsifying, film-forming, water-protecting and protective colloid properties, hydroxyethyl cellulose has been shown to be useful in coatings, medicines, foods, and other fields. Modified cellulose derivatives such as, for example, non-ionic soluble cellulose ethers may be considered polymeric as well based on their backbone of repeating monosaccharides.

While such modified cellulose derivatives may be used as thickening agents alone, they may also be used in combination other known thickening agents, such as any families or individual thickening agents noted herein. By way of example, non-ionic soluble cellulose ethers, preferably comprising hydroxyethyl cellulose may be present in the composition in the range of from about 0.05% to about 5% by weight, preferably from about 0.1% to about 3% by weight, more preferably from about 0.1% to about 0.5% by weight, with from about 0.1 to about 0.3% by weight being even more preferred.

A suitable liquid vehicle for the antiseptic compositions of the present disclosure comprises water, to which acetone or an alcohol, particularly a ($C_1$-$C_4$) alcohol (i.e., a lower alcohol) such as ethanol, 2-propanol, and n-propanol, and mixtures thereof may be added. The use of alcohols in combination with water may enhance initial antimicrobial activity on tissue, or alternatively allow for reductions in surfactant levels. Preferably, the water is purified by any suitable means; more preferably the water or other vehicle is USP grade, including injectable-grade water, i.e., USP grade "water for injection.

Aqueous formulations (of the "non-lower alcohol" type) are typically preferred due at least in part to their gentleness to skin tissue.

In formulating the disclosed topical formulations, it is contemplated that the formulations may further comprise ingredients which, while not having the activity of the above-named ingredients, will aid in the formulation and use of the composition as a whole. Examples of such ingredients are well-known to those of ordinary skill in the art of producing formulations for biological purposes. Examples of these ingredients include such substances as binders, emollients, humectants, preservatives (such as methyl paraben), lubricants, colorants, perfumes, and the like, such as those described in U.S. Pat. No. 5,951,993 (Scholz et al.), fragrances, colorants, tackifiers, plasticizers, and the like. Accordingly, when the surface contemplated is skin, the composition of this disclosure may contain ingredients which are added to known lotions or medicaments, which are physiologically acceptable to skin and which do not contain ingredients which will reverse or retard the action of the irritant-inactivating agent. Surfactants may also be added to disperse the organic components or improve their solubility, inter alia, in the aqueous vehicle. In some aspects, the compositions of the disclosure further comprise glycerin alone or in combination with allantoin. In certain alternative aspects, the compositions of the disclosure further comprise a short chain ($C_1$-$C_4$) alcohol, a benzyl alcohol, an ethanol amine such as triethanol amine, or an emollient such as aloe, or any combination thereof.

In some aspects, the compositions further comprise a surfactant. When the compositions include a surfactant, the surfactant may be anionic, cationic, amphoteric or non-ionic, or combination thereof. Alternatively, the surfactant is anionic or nonionic. In other aspects that include, a surfactant, it is nonionic. Surfactants may play any number of roles in the preparation and/or application of the compositions of the present disclosure, including, for example, improving the solubility or uniformity of dispersion for an iodophor in the aqueous composition. Alternatively or in combination, it may act to assist in reducing surface tension during application to mucosal tissue or skin tissue and/or facilitate drying of the composition on a tissue surface. They may also act to thicken the composition. Numerous examples of this class of molecules are known in the art. In certain aspects, the surfactant acts to assist in emulsifying the more hydrophobic components in the aqueous composition. Preferably, the hydrophilic-lipophilic balance, as calculated by Griffin's method, is in the range of from about 8 to about 15, more preferably from about 8 to about 13, still more preferably from about 9 to about 12. Exemplary surfactants of this type include both anionic and non-ionic surfactants, preferably nonionics. Specific non-limiting examples of non-ionic surfactants of this type are fatty alcohol ethoxylates such as laureth 4. By way of example, the surfactant, preferably laureth-4, is present in the composition in the range of from about 2% to about 8% by weight, preferably from about 3% to about 7% by weight, more preferably from about 3% to about 6% by weight, with from about 3% to about 5% by weight of the composition being even more preferred. In alternative aspects, the surfactant, preferably laureth-4, is present in the composition in the range of from about 1% to about 10% by weight, preferably from about 1% to about 7% by weight, more preferably from about 1% to about 6% by weight. Alternately preferred compositions contain non-ionic surfactants at levels in a range of from about 0.5% to about 7% by weight, preferably from about 1% to about 6% by weight, more preferably from about 1.5% to about 4% by weight, with from about 2% to about 3% by weight of the composition being even more preferred. Additional examples may be found in Kirk Othmer Encyclopedia of Chemical Technology, 3$^{rd}$, Edition, Volume 22, pages 364 and 365.

In yet other aspects, the compositions further comprise an emollient or moisturizer. Moisturizers or emollients are mixtures of chemical compounds specially designed to make the external layers of the skin (epidermis) softer and more pliable. They increase the skin's hydration (water content) by reducing evaporation. Naturally occurring skin lipids and sterols, as well as artificial or natural oils, humectants, emollients, lubricants, etc., may be part of the composition of commercial skin moisturizers. They usually are available as commercial products for cosmetic and therapeutic uses. Emollients can include, for example, fatty alcohols such as $C_{12}$ to $C_{20}$ fatty alcohols, naturally occurring oils such as jojoba oils or products derived from such oils and esters. In some aspects, the moisturizers also assist in viscosity building or modifying. For example, International Flora Technologies, Ltd. Of Chandler, Ariz. provides certain ester products, for example, Floraesters 20, Floraesters 30, and Floraesters 60, based on *Simmondsia chinensis*, that have this dual property capability. By way of example, jojoba esters, such as Floraesters 20, Floraesters K-20W, Floraesters 30, and Floraesters 60, may be present in the compositions of the present disclosure in the range of from about 1% to about 8% by weight, preferably from about 2% to about 7% by weight, more preferably from about 2% to about 6% by weight. Alternatively preferred ranges for any of the Floraester products in compositions of the present disclosure range from about 0.1% to about 6% by weight, preferably from about 0.3% to about 6% by weight, more preferably from about 0.5% to about 6% by weight, still more preferably from about 0.5% to about 4% by weight, yet more preferably from about 0.5% to about 2% by weight. Other exemplary esters of fatty acids and fatty alcohols, saturated and/or unsaturated, from natural or synthetic sources, may be capable of providing one or both of these desirable properties.

Other exemplary emollients include but are not limited to Procetyl 10 PPG-10 cetyl ether, Procetyl 50 PPG-50 cetyl ether, Promyristyl PM-3 PPG-3Myristyl ether, PPG-3 benzyl ether myristate (Crodamol STS of Croda), PEG 20 Almond Glycerides, Probutyl DB-10, Glucam P20, Glucam E-10, Glucam P-10, Glucam E-20, Glucam P-20 distearate, glycerin, propylene glycol, cetyl acetate and acetylated lanolin alcohol (Acetulan), and hydroxylated milk glycerides.

In some other aspects, the compositions further comprise glycerin, a glycerin ether compound, an ethoxylated glycerin compound, or a combination thereof. In aspects where the compositions further comprise glycerin, a glycerin ether compound, an ethoxylated glycerin compound, or a combination thereof, the compound or combination it is typically present as a thickening agent.

In some aspects, the carriers and vehicles include, but are not limited to, micro or nanocapsules, nanoemulsions/submicron emulsions/miniemulsions, solid lipid nanoparticles, multiple emulsions, microemulsions. Vesicular carriers include, but are not limited to, liposomes, niosomes, transfersomes, ethosomes, and aquasomes. Chemical penetration enhancers include, but are not limited to, sulfoxides and similar chemicals, azone, pyrrolidones, fatty acids, essential oils terpenes and terpenoids, oxazolidinones, ureas, water, alcohols, fatty alcohols, and glycerols, and surfactants, see, for example, Mathur, V. et al., Physical and chemical penetration enhancers in transdermal drug delivery system, Asian J. Pharm., 4:173-83 (2010) and Escobar-Chavez, J. J. et al in Pharmacology edited by Luca Gallelli (2012) incorporated herein by reference in their entireties.

In some aspects the topical formulation comprises chemical penetration enhancers. Chemical penetration enhancers include, but are not limited to solvents, surfactants, and chemicals. Examples of solvents include, but are not limited to, water, alcohols such as methanol and ethanol, alkyl methyl sulfoxide, dimethyl sulfoxide, alkyl homologs of methyl sulfoxide such as dimethyl acetamide, and dimethylformamide; pyrrolidones such as 2-pyrrolidone, N-methyl, and 2-pyrrolidone; laurocapran (Azone), propylene glycol, glycerol, silicone fluids and isopropyl palmitate. Examples of surfactants include anionic surfactants including, but not limited to, dioctyl sulphosuccinate, sodium lauryl sulfate and decodecylmethyl sulphoxide; cationic surfactants; and nonionic surfactants such as Pluronic F127 and Pluronic F68. Other chemical penetration enhancers include bile salts such as sodium taurocholate, sodium deoxycholate and sodium tauroglycocholate; binary systems such as propylene glycol/oleic acid and 1,4-butanediol/linoleic acid; and chemicals such as N,N-diethyl-m-toluamide and calcium thioglycolate.

In another aspect the topical formulation comprises chemical penetration enhancers including, but not limited to N-methyl-2-pyrolidone, glycols such as diethylene glycol, propylene glycol and tetraethylene glycol, fatty acids including, but not limited to, lauric, myristic and capric, nonionic surfactants including, but not limited to, polyoxyethylene-2-oleyl ether and polyoxyethylene-2-stearyl ether. In another aspect essential oils of eucalyptus, chenopodium and ylangylang are used. In one aspect L-menthol, terpenes, oxazolidinones, and ureas are used as chemical penetration enhancers see, for example, Pathan, I. B. et al., Tropical J. Pharm. Res., 8(2): 173-179 (2009).

In other aspects the topical formulations comprise common topical ingredients that include, but are not limited to, vehicles such as hydrophobic vehicles, water-miscible vehicle co-solvents, structural matrix formers; suspending, jelling, or viscosity inducing agents, water-in-oil emulsifiers, preservatives, and chelating agents.

In some aspects, hydrophobic vehicles include hydrocarbons such as liquid petrolatum (mineral oil, liquid paraffin, paraffin oil), white petrolatum (petroleum jelly, Vaseline), yellow petrolatum (petroleum jelly), and squalane (perhydrosqualene, spinacane); silicones such as liquid polydimethylsiloxanes (dimethicone, silastic, medical grade silicone oil); alcohols such as lauryl alcohols (1-dodecanol, dodecyl alcohols), myristyl alcohols (tetradecanol, tetradecyl alcohols) cetyl alcohols (hexadecanol, ethal, palmityl alcohols), stearyl alcohols (stenol, cetosteryl alcohols) and oleyl alcohols (ocenol); sterols and sterol esters, including, but not limited to, lanolin (hydrous wool fat, lanum), anhydrous lanolin (wool fat, anhydrous lanum, agnin), and semi synthetic lanolin's; carboxylic acids such as lauric acid, myristic acid, palmitic acid, stearic acid and oleic acid; esters and polyesters including, but not limited to, cholesterol esters (stearate), ethylene glycol monoesters, propylene glycol monoesters, glyceryl monoesters, glyceryl monostearate, sorbitol monoesters, sorbitain monoesters, sorbitol diesters, sorbitan polyesters (spans, arlacels), glyceryl tristearate, lard, almond oil, corn oil, castor oil, cottonseed oil, olive oil, soybean oil, hydrogenated oils, sulfated oils, isopropyl myristate, and isopropyl palmitate; ethers and polyethers such as polyethylene-polypropylene glycols (pluronics).

In another aspect, water-miscible vehicle co-solvents include polyols and polyglycols such as propylene glycol (1,2-propanediol), glycerin (glycerol), liquid polyethylene glycol, solid polyethylene glycol (hard macrogol, carbowax) and 1,2-phenols-hexanetriol, sorbitol solution 70%; esters and polyesters such as polyoxyethylene sorbitain monoesters (stearate-tweens) and polyoxy ethylene sorbitan polyesters (tweens); ethers and polyethers, including but not limited to, polyethylene glycol monocetyl ether (cetomacrogol 1000) and polyethylene-polypropylene glycols (pluronics).

In other aspects, structural matrix formers include but are not limited to hydrocarbons, silicones, polyols and polyglycols, alcohols, sterols and sterol esters, carboxylic acids, esters and polyesters. Examples of hydrocarbons include, but are not limited to, white petrolatum (petroleum jelly, Vaseline), yellow petrolatum (petroleum jelly), paraffin (paraffin wax, hard paraffin), microcrystalline wax and ceresin (mineral wax, purified ozokerite). Examples of silicones include, but are not limited to fumed silica (cab-O-sil), bentonite (colloidal aluminum silicate) and veegum (colloidal magnesium aluminum silicate). Examples of polyols and polyglycols include, but are not limited to solid polyethylene glycol (hard macrogol, carbowax). Examples of alcohols include, but are not limited to, cetyl alcohols (hexadecanol, ethal, palmityl alcohols) and stearyl alcohols (stenol, cetosteryl alcohols). Examples of sterols and sterol esters include, but are not limited to, cholesterol (cholesterin), lanolin (hydrous wool fat, lanum), anhydrous lanolin (wool fat, anhydrous lanum, and agnin), and semi-synthetic lanolin's. Examples of carboxylic acids include, but are not limited to, lauric acid, myristic acid, palmitic acid, stearic acid, and oleic acid. Examples of esters and polyesters include, but are not limited to, bees wax, white bees wax (bleached bees wax), carnauba wax, myricin, cholesterol esters (stearate), polyoxyethylene sorbitain, monoesters (stearate-tweens), lard, and hydrogenated oils.

In another aspect suspending, jelling or viscosity inducing agents include silicones, polycarboxylates, polysulfates, polysaccharides and other compounds. Silicones include, but are not limited to, uhmed silica (cab-O-sil), bentonite (colloidal aluminum silicate) and veegum (colloidal magnesium aluminum silicate). Polycarboxylates, polysulfates and polysaccharides include, but are not limited to, agar, alginates, carrageen, acacia, tragacanth, methylcellulose, carboxy methylcellulose, hydroxy ethyl cellulose, carboxy vinyl polymer, gelatin, pectin, xanthan, and polyacrylic acid. Other compounds include, but are not limited to, ethanolamine and triethanolamine.

In some aspects, water-in-oil (w/o) emulsifiers include but are not limited to, sterols and sterol esters, carboxylic acids, ether and polyethers. Sterols and sterol esters include, but are not limited to, cholesterol (cholesterin), lanolin (hydrous wool fat, lanum), anhydrous lanolin (wool fat, anhydrous lanum, agnin), and semi-synthetic lanolin's. Carboxylic acids include, but are not limited to, the $Na^+$, $K^+$ and ethanolamine salts of lauric acid, myristic acid, palmitic acid, stearic acid, and oleic acid. Ethers and polyethers include, but are not limited to, polyethylene-polypropylene glycols (pluronics).

In another aspect, oil-in-water (o/w) emulsifiers include, but are not limited to, esters and polyesters, ethers and polyethers and other miscellaneous reagents. Esters and polyesters, include, but are not limited to, polyoxyethylene sorbitain monoesters (stearate-tweens), polyoxy ethylene esters (stearate-polyethylene glycol monoesters, Myrj), and polyoxy ethylene sorbitan polyesters (tweens). Ethers and polyethers, but are not limited to, polyethylene glycol monocetyl ether (cetomacrogol 1000) and polyethylene-polypropylene glycols (pluronics). Other miscellaneous reagents, but are not limited to, sodium lauryl sulfate, Borax (sodium borate), ethanolamine and triethanolamine.

In one aspect, chelating agents include but are not limited to, citric acid and edetic acid. The chelating agents can be combined with buffers produced from reagents such as phosphoric acid, $NaH_2PO_4$, glycine, acetic acid, triethanolamine and boric acid. In another aspect, chelating agents can be combined with humectants including, but not limited to, glycerin, propylene glycol, glyceryl triacetate, sorbitol, xylitol, maltitol, polydextrose, *quillaia*, lactic acid, urea, and lithium chloride.

In one aspect, ointments comprise therapeutic composition in ointment bases. Ointment bases are typically classified by the USP into four general groups (a) hydrocarbon bases including but not limited to, petrolatum, USP; white petrolatum, USP; yellow petrolatum, USP; white petrolatum, USP; (b) absorption bases that include water-in-oil emulsions (c) water-removable bases that include hydrophilic ointment, USP; and (d) water-soluble bases such as polyethylene glycol ointment, NF.

In another aspect, creams comprise therapeutic composition dissolved or suspended in water removable or emollient bases. Creams are classified as water-in-oil or oil-in-water. There are several types of creams including but not limited to cleaning and cold cream or lotion, vanishing and foundation cream, night and massage cream, hand and body cream, all purpose cream, and moisturizing cream. Examples of cream bases include (a) cream base, w/o (rose water ointment) oleaginous phase including but not limited to, spermaceti, white wax, almond oil, sodium borate and an aqueous phase including but not limited to, sodium borate, stronger rose water, NF, and water (b) cream base o/w including an oleaginous phase including but not limited to, stearyl alcohol, beeswax and sorbitan monooleate, and an aqueous phase including but not limited to, sorbitol solution, polysorbate 80, methyl paraben, and water (c) cream base, o/w (vanishing cream) including an oleaginous phase including, but not limited to, stearic acid, stearyl alcohol, cetyl alcohol and an aqueous phase including but not limited to, glycerin, methyl paraben, propyl paraben, potassium hydroxide, and water.

In another aspect, a disclosed topical formulation can be formulated as a paste or gel. Examples of gelling agents include, but are not limited to, synthetic macromolecules such as Carbomer 934 and cellulose derivatives such as carboxymethylcellulose and hydroxypropyl methylcellulose. In one aspect, gels include single phase and double phase gels.

In one aspect, a disclosed topical formulation can be formulated as a jelly. In one aspect, jellies are water-soluble bases typically prepared from natural gums such as tragacanth, pectin, alginate and boroglycerin or from synthetic derivatives of natural substances such as methylcellulose and carboxymethylcellulose.

In some aspects, a disclosed topical formulation can be formulated as a lotion or liniment. Examples of lotions include, but are not limited to, hand lotions, face lotions and body lotions. Lotions can comprise alcohols such as ethyl alcohol, antiseptics, emollients and hemostypic substances. In another aspect, lotions comprise extract of witchhazel, menthol, glycerin, boric acid, alum, potassium oxyquinoline; sulfate and chloroform.

In some aspects, a disclosed topical formulation can be formulated as a solution. In an aspect, solvents used to prepare solutions include, but are not limited to, water, ethyl alcohol and propylene glycol.

In another aspect, a disclosed topical formulation can be formulated as an emulsion. In some aspects, emulsions include, but are not limited to, water-in-oil, oil-in-water, water-in-oil-in-water and oil-in-water-in-oil.

In one aspect, a disclosed topical formulation can be formulated as a suspension. In some aspects, suspensions include, but are not limited to, flocculated and deflocculated suspensions.

In some aspects, a disclosed topical formulation can be formulated in the form of an aerosol. In one aspect, topical aerosols comprise hydrocarbons (propane, butane and isobutene), and compressed gases such as nitrogen, carbon dioxide and nitrous oxide.

In some aspects, a disclosed topical formulation can comprise a healing ointment such as Aquaphor®. See, U.S. Pat. No. 7,976,854 to Hattendorf et al. incorporated herein in its entirety.

In some aspects the therapeutic composition can be formulated with VersaBase Cream, VersaBase Foam, VersaBase Gel, VersaBase Lotion, or VersaBase Shampoo.

In some aspects, a disclosed topical formulation can be formulated as a spot-on formulation. See, U.S. Pat. No. 7,531,186 to Boeckh et al. incorporated herein in its entirety. In one aspect, the topical formulation comprises the therapeutic composition, a liquid carrier vehicle and optionally a crystallization inhibitor. In some aspects, the liquid carrier vehicle comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethylene glycol monoethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of ethanol, isopropanol or methanol; and optionally a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

In certain aspects, a disclosed topical formulation comprises: a disclosed therapeutic composition, a pharmaceutically acceptable dipolar aprotic solvent or an acid; and a pharmaceutically acceptable aqueous secondary solvent. See, U.S. Pat. No. 6,844,004 to Anderson herein incorporated by reference. In some aspects, the acid is a carboxylic acid and is exemplified by acetic acid. In other aspects, the acid is hydrochloric acid. In some aspects, the aqueous secondary solvent is a surfactant. Surfactants are well known in the art and are organic lipid compounds that are normally produced by the lung tissue and help with the opening of the alveolar constrictions during breathing. Surfactants are also commercially available. In still other aspects the aqueous secondary solvent is an aqueous lipid emulsion. The aqueous lipid emulsion can comprise a lipid component that includes at least one vegetable oil and at least one fatty acid. Such a lipid component can comprise at least about 5% by weight soybean oil and at least about 50% by weight fatty acids. In some aspects, the lipids in the composition are preferably present in a form other than liposomes, for example, at least about 50% by weight of the lipid is not in the form of liposomes, more preferably a least about 75%, and most preferably at least about 95%. In other aspects the secondary solvent can be water, a saline solution, or a dextrose solution. In some aspects, the composition further comprises an ointment and/or a cream base. The ointment base can comprise one or more of petrolatum, mineral oil, ceresin, lanolin alcohol, panthenol, glycerin, bisabolol, cocoa butter and the like. The ointment or cream can be any commonly known commercially available ointments or creams such as Aquaphor™ or Eucerin™.

In various aspects, the disclosed topical formulations can further comprise additional ingredients that may be provided in order to facilitate scar reduction, such as but not limited to: levocetirizine, pentoxyifylline, gabapentin, tranilast, vitamin E, Emu Oil, salicylic acid, tretinoin (retinoic acid), or combinations thereof. Levocetirizein is an antihistamine used to decrease the itching associated with healing skin. During the normal healing response mast cells play a vital role. It has been found that in the formation of some keloid and hypertrophic scars there is an abnormally high amount of mast cells involved. The mast cells can release histamine causing the healing skin to itch. Levocetiririzine will decrease collagen production at higher topical concentrations. Pentoxyifylline, which is a blood viscosity reducer agent and acts to decreases collagen production. Gabapentin, which is an inhibition of excitatory neurotransmitters and decreases pain caused by firing neurons. Tranilast, which is an anti-allergic and may be an indication for keloid and hypertrophic scar. Vitamin E, which promotes skin elasticity thus minimizing the tissue tearing. Emu Oil, which is derived from emu fat and claims to have anti-inflammatory and skin penetrating properties. Salicylic Acid, which is a peeling agent for the treatment of acne, as it removes intercellular lipids that are covalently linked to the cornified envelope surrounding cornified epitheliod cells. Tretinoin (retinoic acid), which is a metabolite of vitamin A (retinol) and responsible for most of the activity of vitamin A and is used for acne treatment, anti-wrinkle, and stretch marks.

In various aspects, the disclosed topical formulations can comprise a preservative. As used herein, the terms "preservative system" or "preservatives" include all preservatives approved for use in pharmaceutical, food and beverage compositions including, without limitation, such known chemical preservatives as benzoates including sodium, calcium, and potassium benzoate, sorbates including sodium, calcium, and potassium sorbate, citrates including sodium citrate and potassium citrate, polyphosphates including sodium hexametaphosphate (SHMP), and mixtures thereof, and antioxidants such as ascorbic acid, EDTA, BHA, BHT, TBHQ, dehydroacetic acid, dimethyldicarbonate, ethoxyquin, heptylparaben, and combinations thereof. Preservatives can be used in amounts not exceeding mandated maximum levels. In still another aspect, preservatives include antimicrobials such as benzalkonium chloride, benzoic acid, benzyl alcohol, bronopol, chlorhexidine, chlorocresol, imidazolidinyl urea, paraben esters, phenol, phenoxyethanol, potassium sorbate, and sorbic acid. Preservatives also include antioxidants such as α-tocopherol, ascorbic acid, ascorbyl palmitate, butylated hydroxyanisole, sodium ascorbate, and sodium metabisulfite.

In various aspects, the disclosed formulations can optionally further comprise an additional ingredient, which may be an inactive ingredient or an inactive ingredient. In a further aspect, an optional additional ingredient can be caffeine, saw palmetto extract, or combinations thereof.

In some aspects, the disclosed formulations can optionally comprise caffeine present in an amount of from about 0.0001 wt % to about 0.010 wt %. In a further aspect, the disclosed formulations can optionally comprise caffeine present in an amount of from about 0.001 wt % to about 0.007 wt %. In a still further aspect, the disclosed formulations can optionally comprise caffeine present in an amount of from about 0.001 wt % to about 0.005 wt %. In a yet further aspect, the disclosed formulations can optionally comprise caffeine present in an amount of from about 0.001 wt % to about 0.003 wt %. In various aspects, the disclosed formulations can optionally comprise caffeine present in an amount of about 0.0001 wt %, about 0.0002 wt %, about 0.0003 wt %, about 0.0004 wt %, about 0.0005 wt %, about 0.0006 wt %, about 0.0007 wt %, about 0.0008 wt %, about 0.0009 wt %, about 0.0010 wt %, about 0.0011 wt %, about 0.0012 wt %, about 0.0013 wt %, about 0.0014 wt %, about 0.0015 wt %, about 0.0016 wt %, about 0.0017 wt %, about 0.0018 wt %, about 0.0019 wt %, about 0.0020 wt %, about 0.0021 wt %, about 0.0022 wt %, about 0.0023 wt %, about 0.0024 wt %, about 0.0025 wt %, about 0.0026 wt %, about 0.0027 wt %, about 0.0028 wt %, about 0.0029 wt %, about 0.0030 wt %, about 0.0031 wt %, about 0.0032 wt %, about 0.0033 wt %, about 0.0034 wt %, about 0.0035 wt %, about 0.0036 wt %, about 0.0037 wt %, about 0.0038 wt %, about 0.0039 wt %, about 0.0040 wt %, about 0.0041 wt %, about 0.0042 wt %, about 0.0043 wt %, about 0.0044 wt %, about 0.0045 wt %, about 0.0046 wt %, about 0.0047 wt %, about 0.0048 wt %, about 0.0049 wt %, about 0.0050 wt %, about 0.0051 wt %, about 0.0052 wt %, about 0.0053 wt %, about 0.0054 wt %, about 0.0055 wt %, about 0.0056 wt %, about 0.0057 wt %, about 0.0058 wt %, about 0.0059 wt %, about 0.0060 wt %, about 0.0061 wt %, about 0.0062 wt %, about 0.0063 wt %, about 0.0064 wt %, about 0.0065 wt %, about 0.0066 wt %, about 0.0067 wt %, about 0.0068 wt %, about 0.0069 wt %, about 0.0070 wt %, about 0.0071 wt %, about 0.0072 wt %, about 0.0073 wt %, about 0.0074 wt %, about 0.0075 wt %, about 0.0076 wt %, about 0.0077 wt %, about 0.0078 wt %, about 0.0079 wt %, about 0.0080 wt %, about 0.0081 wt %, about 0.0082 wt %, about 0.0083 wt %, about 0.0084 wt %, about 0.0085 wt %, about 0.0086 wt %, about 0.0087 wt %, about 0.0088 wt %, about 0.0089 wt %, about 0.0090 wt %, about 0.0091 wt %, about 0.0092 wt %, about 0.0093 wt %, about 0.0094 wt %, about 0.0095 wt %, about 0.0096 wt %, about 0.0097 wt %, about 0.0098 wt %, about 0.0099 wt %, about 0.010 wt %; or any range encompassed by the foregoing values; or any combination of the foregoing values.

In some aspects, the disclosed formulations can optionally comprise saw palmetto extract present in an amount of from about 0.01 wt % to about 50 wt %. The saw palmetto extract can be any suitable nutraceutical or cosmeceutical grade saw palmetto extract. In a further aspect, the disclosed formulations can optionally comprise caffeine present in an amount of from about 0.1 wt % to about 30 wt %. In a still further aspect, the disclosed formulations can optionally comprise caffeine present in an amount of from about 1 wt % to about 10 wt %. In a yet further aspect, the disclosed formulations can optionally comprise caffeine present in an amount of from about 1 wt % to about 8 wt %. In various aspects, the disclosed formulations can optionally comprise caffeine present in an amount of about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.10 wt %, about 0.11 wt %, about 0.12 wt %, about 0.13 wt %, about 0.14 wt %, about 0.15 wt %, about 0.16 wt %, about 0.17 wt %, about 0.18 wt %, about 0.19 wt %, about 0.20 wt %, about 0.21 wt %, about 0.22 wt %, about 0.23 wt %, about 0.24 wt %, about 0.25 wt %, about 0.26 wt %, about 0.27 wt %, about 0.28 wt %, about 0.29 wt %, about 0.30 wt %, about 0.31 wt %, about 0.32 wt %, about 0.33 wt %, about 0.34 wt %, about 0.35 wt %, about 0.36 wt %, about 0.37 wt %, about 0.38 wt %, about 0.39 wt %, about 0.40 wt %, about 0.41 wt %, about 0.42 wt %, about 0.43 wt %, about 0.44 wt %, about 0.45 wt %, about 0.46 wt %, about 0.47 wt %, about 0.48 wt %, about 0.49 wt %, about 0.50 wt %, about 0.51 wt %, about 0.52 wt %, about 0.53 wt %, about 0.54 wt %, about 0.55 wt %, about 0.56 wt %, about 0.57 wt %, about 0.58 wt %, about 0.59 wt %, about 0.60 wt %, about 0.61 wt %, about 0.62 wt %, about 0.63 wt %, about 0.64 wt %, about 0.65 wt %, about 0.66 wt %, about 0.67 wt %, about 0.68 wt %, about 0.69 wt %, about 0.70 wt %, about 0.71 wt %, about 0.72 wt %, about 0.73 wt %, about 0.74 wt %, about 0.75 wt %, about 0.76 wt %, about 0.77 wt %, about 0.78 wt %, about 0.79 wt %, about 0.80 wt %, about 0.81 wt %, about 0.82 wt %, about 0.83 wt %, about 0.84 wt %, about 0.85 wt %, about 0.86 wt %, about 0.87 wt %, about 0.88 wt %, about 0.89 wt %, about 0.90 wt %, about 0.91 wt %, about 0.92 wt %, about 0.93 wt %, about 0.94 wt %, about 0.95 wt %, about 0.96 wt %, about 0.97 wt %, about 0.98 wt %, about 0.99 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt %, about 6.0 wt %, about 6.1 wt %, about 6.2 wt %, about 6.3 wt %, about 6.4 wt %, about 6.5 wt %, about 6.6 wt %, about 6.7 wt %, about 6.8 wt %, about 6.9 wt %, about 7.0 wt %, about 7.1 wt %, about 7.2 wt %, about 7.3 wt %, about 7.4 wt %, about 7.5 wt %, about 7.6 wt %, about 7.7 wt %, about 7.8 wt %, about 7.9 wt %, about 8.0 wt %, about 8.1 wt %, about 8.2 wt %, about 8.3 wt %, about 8.4 wt %, about 8.5 wt %, about 8.6 wt %, about 8.7 wt %, about 8.8 wt %, about 8.9 wt %, about 9.0 wt %, about 9.1 wt %, about 9.2 wt %, about 9.3 wt %, about 9.4 wt %, about 9.5 wt %, about 9.6 wt %, about 9.7 wt %, about 9.8 wt %, about 9.9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, about 50 wt %; or any range encompassed by the foregoing values; or any combination of the foregoing values.

In various aspects, the disclosed topical formulations can further comprise conventional cosmetic adjuvants, such as dyes, opacifiers (e.g., titanium dioxide), pigments and fragrances.

In various aspects, the disclosed topical formulations can further comprise a safe and effective amount of a penetration enhancing (or reducing) agent. By "safe and effective amount" is meant an amount sufficient to enhance (or reduce) the penetration of the disclosed therapeutic compositions extracts into the skin, but not so much as to cause any side effects or skin reactions. Penetration enhancers can be provided in amounts from about 1% to about 10% of the topical formulation.

In a further aspect, exemplary skin penetration enhancers include sulfoxides such as dimethylsulfoxide (DMSO) and the like; cyclic amides such as 1-dodecylazacycloheptane-2-one (AZONE, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, α-pinene, β-carene, α-terpineol, carvol, carvone, menthone, limonene oxide, α-pinene oxide, eucalyptus oil, and the like. Also suitable as skin penetration enhancers are organic acids and esters such as salicyclic acid, methyl salicylate, citric acid, succinic acid, and the like.

In various aspects, the disclosed topical formulations can be applied using a vacuum actuated applicator. In some aspects, the vacuum actuated applicator is designed to provide blocking of UV light and minimize oxidation.

Methods of Using the Disclosed Formulations
@@@

In various aspects, the disclosed topical formulations can be applied to the scalp and/or hair once per day or in multiple applications applied in various fractions of a 24 hour period. In a further aspect, disclosed topical formulations can be applied to the scalp and/or hair once per day, twice per day, three times per day, four times per day, five times per day, or six times per day.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1. An exemplary disclosed formulation was prepared comprising: (a) active ingredients: azelaic acid 0.325 wt %, minoxidil 15 wt %, finasteride 0.2 wt %, and dutasteride 0.01% w/v %; and (b) compound components: ethoxy Di-Glycol (6 ml per 100 gm of final weight), specific gravity=1.05; propylene glycol (3.5 ml per 100 gm of final weight), specific gravity=1.1; VersaBase Gel® (11 gm per 100 gm of final weight); heavy cream base (22.5 gm per 100 gm of final weight); and silicone base (27.75 gm per 100 gm of final weight). The silicone base used was either Pracasil® (PCCA) or Scar Care Base Enhanced (Letco Medical).

The subject noted that the exemplary formulation did not have the oily viscosity associated with conventional topical formulations that resulted in a wetted hair look when applied. The subject further noted that the exemplary formulation appeared to have an immediate nourishing effect on their hair with almost immediate cessation of hair loss stopped and growth of new dark thicker hair with a healthy looking appearance. Moreover, it was noted that it was not necessary to apply the cream twice a day as one application daily was found to be sufficient. The subject further observed that conventional formulations often were associated with scalp itching after about 12 hours. In contrast, the exemplary formulation was not associated with scalp itching. Moreover, the exemplary formulation appeared to provide a healthy scalp with little or no appearance of flaking skin.

Example 2. An exemplary disclosed formulation was prepared comprising: (a) active ingredients: azelaic acid 0.325 wt %, minoxidil 15 wt %, finasteride 0.2 wt %, and dutasteride 0.01% w/v %; (b) other ingredients: caffeine 0.0025 wt %; and (c) compound components: ethoxy diglycol (6 ml per 100 gm of final weight), specific gravity=1.05; propylene glycol (3.5 ml per 100 gm of final weight), specific gravity=1.1; VersaBase Gel® (PCCA; 10 gm per 100 gm of final weight); HRT cream base (Letco Medical; 21.5 gm per 100 gm of final weight); and silicone base (26.75 gm per 100 gm of final weight). The silicone base used was either Pracasil® (PCCA) or Scar Care Base Enhanced (Letco Medical).

The subject noted similar results as obtained in Example 1. In particular, the subject note that the exemplary formulation had the following characteristics: (a) the exemplary formulation stays in place on the scalp and does not run off onto forehead or cheek areas; (b) the exemplary formulation does not require two applications per day, one is enough to last 24 or more hours before reapplication; (c) the viscosity of the exemplary formulation provides for extended contact of the active ingredients with scalp; and (d) the exemplary formulation appears to provide scalp healing benefits such as improved overall scalp health, decrease or complete itch relief, increased blood flow, and improved hair growth. In contrast, conventionally available formulations having 5-15 wt % minoxidil were found by the subject to be quite oily, which allowed it to better stay in place on the scalp, but it transferred onto the hair it made the hair look like it was oily with an extended period of time required for the conventional formulation to dry to the point that the hair had a more natural, non-oily appearance.

It should be emphasized that the above-described aspects of the present disclosure are merely possible examples of implementations set forth for a clear understanding of the principles of the disclosure. Many variations and modifications may be made to the above-described aspect(s) without departing substantially from the spirit and principles of the disclosure. All such modifications and variations are intended to be included herein within the scope of this disclosure and protected by the following claims.

What is claimed is:

1. A topical formulation for treatment of hair loss, promotion of scalp health, and/or to increase hair growth, the formulation comprising:
    a therapeutic composition comprising therapeutically effective amounts of azelaic acid, minoxidil, finasteride, and dutasteride;
    and a compounding agent comprising (a) a silicone base comprising (i) cyclopentasiloxane, a dimethicone, C30-45 alkyl cetearyl dimethicone crosspolymer, or any combination thereof and (ii) a cross-linked siloxane and (b) an oil comprising oleic acid, linoleic acid, or a combination thereof,
wherein the topical formulation is a gel or cream.

2. The topical formulation of claim 1, wherein the therapeutically effective amounts of azelaic acid, minoxidil, finasteride, and dutasteride comprise:
    about 0.100 wt % to about 0.500 wt % azelaic acid;
    about 10 wt % to about 20 wt % minoxidil;
    about 0.05 wt % to about 0.50 wt % finasteride; and
    about 0.001 wt % to about 0.030 wt % dutasteride;
wherein the wt % of a component is based on the total weight of the therapeutic composition and the compounding agent.

3. The topical formulation of claim 2, wherein the therapeutically effective amounts of azelaic acid, minoxidil, finasteride, and dutasteride comprise:
    about 0.300 wt % to about 0.400 wt % azelaic acid;
    about 12 wt % to about 17 wt % minoxidil;
    about 0.10 wt % to about 0.30 wt % finasteride; and
    about 0.005 wt % to about 0.015 wt % dutasteride;
wherein the wt % of a component is based on the total weight of the therapeutic composition and the compounding agent.

4. The topical formulation of claim 2, wherein the therapeutically effective amounts of azelaic acid, minoxidil, finasteride, and dutasteride comprise:
    about 0.325 wt % azelaic acid;
    about 15 wt % minoxidil;
    about 0.20 wt % finasteride; and
    about 0.010 wt % dutasteride;
wherein the wt % of a component is based on the total weight of the therapeutic composition and the compounding agent.

5. The topical formulation of claim 1, wherein the compounding agent further comprises ethoxy diglycol, propylene glycol, a gel base, a cream base, or combinations thereof.

6. The topical formulation of claim 5, wherein the compound agent comprises:
    about 1 vol/wt % to about 10 vol/wt % ethoxy diglycol;
    about 1 vol/wt % to about 10 vol/wt % propylene glycol;
    about 5 wt % to about 20 wt % of a gel base for gel-cream emulsions;
    about 15 wt % to about 35 wt % of a cream base; and
    about 15 wt % to about 50 wt % of the silicone base;
wherein the wt % of a component is based on the total weight of the therapeutic composition and the compounding agent; and
wherein the vol/wt % of a component is based on the total weight of the therapeutic composition and the compounding agent.

7. The topical formulation of claim 5, wherein the compounding agent comprises:
    about 4 vol/wt % to about 6 vol/wt % ethoxy diglycol;
    about 2.5 vol/wt % to about 4.5 vol/wt % propylene glycol;
    about 8 wt % to about 14 wt % of a gel base for gel-cream emulsions;
    about 20 wt % to about 30 wt % of a cream base; and
    about 20 wt % to about 30 wt % of the silicone base;
wherein the wt % of a component is based on the total weight of the therapeutic composition and the compounding agent; and
wherein the vol/wt % of a component is based on the total weight of the therapeutic composition and the compounding agent.

8. The topical formulation of claim 5, wherein the compound agent comprises:
    about 6 vol/wt % ethoxy diglycol;
    about 3.5 vol/wt % propylene glycol;
    about 11 wt % of a gel base for gel-cream emulsions;
    about 21 wt % to about 23 wt % of a cream base; and
    about 26 wt % to about 29 wt % of the silicone base;
wherein the wt % of a component is based on the total weight of the therapeutic composition and the compounding agent; and
wherein the vol/wt % of a component is based on the total weight of the therapeutic composition and the compounding agent.

9. The topical formulation of claim 5, wherein gel base for gel-cream emulsions comprises water, ammonium acryloyldimethyltaurate copolymer, aloe barbadensis leaf juice powder, allatoin, disodium EDTA, methylchloroisothiazolinone, methylisothiazolinone, or combinations thereof.

10. The topical formulation of claim 1, wherein the silicone base has a pH of about 5.5 to about 6.5.

11. The topical formulation of claim 1, wherein the silicone base has a pH of about 5.9 to about 6.1.

12. The topical formulation of claim 1, wherein the compounding agent further comprises an *Carapa guaianensis* seed oil, macadamia nut oil, laureth-4, PEG 30 dipolyhydroxystearate, or combinations thereof.

13. The topical formulation of claim 1, further comprising caffeine, saw palmetto extract, or a combination thereof.

14. The topical formulation of claim 13, wherein the caffeine is present in an amount from about 0.0001 wt % to about 0.007 wt %.

15. The topical formulation of claim 13, wherein the saw palmetto extract is present in an amount from about 0, 1 wt % to about 15 wt %.

16. A method to treat hair loss comprising applying the topical formulation of claim 1 to the hair and/or scalp of a subject.

17. A method to enhance hair growth comprising applying the topical formulation of claim 1 to the hair and/or scalp of a subject.

18. A method for improving scalp health comprising applying the topical formulation of claim 1 to the scalp of a subject.

19. The topical formulation of claim 1, wherein the oil comprises pracaxi oil.

20. The topical formulation of claim 1, further comprises an antioxidant.

21. The topical formulation of claim 1, wherein the topical formulation comprises from about 10 wt % to about 20 wt % minoxidil.

22. The topical formulation of claim 1, wherein the silicone base comprises cyclopentasiloxane, a dimethicone, C30-45 alkyl cetearyl dimethicone crosspolymer, and a cross-linked siloxane.

23. The topical formulation of claim 1, wherein the silicone base comprises cyclopentasiloxane, a dimethicone, C30-45 alkyl cetearyl dimethicone crosspolymer, or and a cross-linked siloxane, and minoxidil is from 10 wt % to about 20 wt % of the topical formulation.

24. The topical formulation of claim 1, wherein the silicone base is from 15 wt % to 50 wt % of the topical formulation.

25. The topical formulation of claim 1, wherein the silicone base is from 20 wt % to 30 wt % of the topical formulation.

26. The topical formulation of claim 1, wherein the silicone base is from 15 wt % to 50 wt % of the topical formulation and minoxidil is from 10 wt % to about 20 wt % of the topical formulation.

* * * * *